US012575903B2

(12) United States Patent
Scholan et al.

(10) Patent No.: US 12,575,903 B2
(45) Date of Patent: *Mar. 17, 2026

(54) CONTROL SYSTEM FOR SURGICAL ROBOT SYSTEM WITH SAFETY DEVICE

(71) Applicant: CMR Surgical Limited, Cambridge (GB)

(72) Inventors: Andrew Murray Scholan, Cheshunt (GB); Adam Peter Sutton, Ely (GB); Paul Christopher Roberts, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 356 days.

This patent is subject to a terminal disclaimer.

(21) Appl. No.: 18/043,118

(22) PCT Filed: Aug. 31, 2021

(86) PCT No.: PCT/GB2021/052249
§ 371 (c)(1),
(2) Date: Feb. 27, 2023

(87) PCT Pub. No.: WO2022/043716
PCT Pub. Date: Mar. 3, 2022

(65) Prior Publication Data
US 2025/0120777 A1     Apr. 17, 2025

(30) Foreign Application Priority Data

Aug. 31, 2020    (GB) ...................................... 2013656
Aug. 31, 2020    (GB) ...................................... 2013657

(51) Int. Cl.
*A61B 34/37*        (2016.01)
*B25J 9/16*         (2006.01)
(Continued)

(52) U.S. Cl.
CPC ............. *A61B 34/37* (2016.02); *B25J 9/1674* (2013.01); *B25J 9/1689* (2013.01);
(Continued)

(58) Field of Classification Search
CPC ....... A61B 34/37; B25J 9/1674; B25J 9/1689; G05B 19/4155; H04L 43/0817
(Continued)

(56) References Cited

U.S. PATENT DOCUMENTS

2007/0147385 A1    6/2007    Druke et al.
2008/0140088 A1    6/2008    Orban, III
(Continued)

FOREIGN PATENT DOCUMENTS

CA        3090336 A1      8/2019
CN        103192388 A     7/2013
(Continued)

OTHER PUBLICATIONS

International Search Report and Written Opinion PCT Application No. PCT/GB2021/052248 Date of Mailing: Dec. 8, 2021 (18 pages).
(Continued)

*Primary Examiner* — Dominic D Saltarelli
(74) *Attorney, Agent, or Firm* — Finch & Maloney PLLC

(57)                ABSTRACT

A control system for controlling a surgical robot system, the surgical robot system comprising a surgical robot, the surgical robot comprising a base, and an arm extending from the base to an attachment for an instrument, the arm comprising a plurality of joints whereby the configuration of the arm can be altered, the control system comprising: a main controller configured to: receive communications identifying inputs from an operator of the surgical robot; generate control signals for controlling the movement of the surgical robot arm based on the inputs; and send communications to (Continued)

the surgical robot identifying the control signals; and a safety device situated such that communications to and from the main controller pass through the safety device, the safety device being operable to selectively filter the communications to and/or from the main controller.

20 Claims, 10 Drawing Sheets

(51) Int. Cl.
    *G05B 19/4155*      (2006.01)
    *H04L 43/0817*      (2022.01)

(52) U.S. Cl.
    CPC ...... *G05B 19/4155* (2013.01); *H04L 43/0817*
    (2013.01); *G05B 2219/40415* (2013.01)

(58) Field of Classification Search
    USPC ........................................................ 375/350
    See application file for complete search history.

(56) References Cited

U.S. PATENT DOCUMENTS

| | | |
|---|---|---|
| 2009/0198379 A1 | 8/2009 | Komuro et al. |
| 2014/0005682 A1 | 1/2014 | Worrell et al. |
| 2015/0112481 A1 | 4/2015 | Burns et al. |
| 2015/0272575 A1 | 10/2015 | Leimbach et al. |
| 2015/0295949 A1 | 10/2015 | Chizeck et al. |
| 2015/0342689 A1 | 12/2015 | Kamon et al. |
| 2016/0256184 A1 | 9/2016 | Shelton, IV et al. |
| 2017/0007336 A1 | 1/2017 | Tsuboi et al. |
| 2018/0168622 A1 | 6/2018 | Shelton, IV et al. |
| 2019/0083190 A1 | 3/2019 | Graves et al. |
| 2019/0192238 A1 | 6/2019 | Tsuboi |
| 2019/0192246 A1 | 6/2019 | Xu et al. |
| 2020/0352664 A1 | 11/2020 | King et al. |
| 2020/0391381 A1 | 12/2020 | Ma et al. |
| 2022/0039889 A1 | 2/2022 | Desai |

FOREIGN PATENT DOCUMENTS

| | | |
|---|---|---|
| CN | 103381605 A | 11/2013 |
| CN | 106272554 A | 1/2017 |

OTHER PUBLICATIONS

International Search Report and Written Opinion PCT Application No. PCT/GB2021/052249 Date of Mailing: Dec. 3, 2021 (15 pages).

Search Report for GB Application No. GB2013656.0 Date of Mailing Feb. 16, 2021 (4 pages).

Search Report for GB Application No. GB2013657.8 Date of Mailing Feb. 16, 2021 (3 pages).

M. Gunther, Posted Answer to "Node Name Collision with Multiple Talker Node Instances", ROS Answers Bog, May 6, 2012.

CONTROL SYSTEM FOR SURGICAL ROBOT SYSTEM WITH SAFETY DEVICE

CROSS-REFERENCE TO RELATED APPLICATIONS

This application claims priority under 35 U.S.C. § 371 as a national stage application of PCT Application No. PCT/GB2021/052249, filed Aug. 31, 2021, which claims priority to GB Application No: 2013656.0, filed Aug. 31, 2020, and GB Application No. 2013657.8, filed Aug. 31, 2020. Each of the foregoing applications is hereby incorporated herein by reference in its entirety.

BACKGROUND

It is known to use robots for assisting and performing surgery. FIG. 1 illustrates an example surgical robot system 100 comprising a surgical robot 102 which consists of a base 104, an arm 106, and an instrument 108. The base 104 supports the robot, and is itself attached rigidly to, for example, the operating theatre floor, the operating theatre ceiling or a trolley. The arm 106 extends between the base 104 and the instrument 108. The arm 106 is articulated by means of multiple flexible joints 110 along its length, which are used to locate the surgical instrument in a desired location relative to the patient. The surgical instrument is attached to the distal end 112 of the robot arm. The surgical instrument penetrates the body of the patient 114 at a port 116 so as to access the surgical site. At its distal end, the instrument comprises an end effector 118 for engaging in a medical procedure.

The surgical robot 102 is controlled remotely by an operator (e.g. surgeon) via an operator console 120 that may be located in the same room (e.g. operating theatre) as the surgical robot 102 or remotely from it. The operator console 120 may comprise input devices 122, 124 for controlling the state of the arm 106 and/or instrument 108 attached thereto. The input devices 122, 124 may be, for example, handgrips or hand controllers (e.g. one for each hand), with one or more buttons thereon, mounted on parallelogram linkages. The operator console 120 may also comprise a display 126. The display 126 may be arranged to be visible to an operator (e.g. surgeon) operating the input devices 122, 124. The display 126 may be used to display a video stream of the surgical site (e.g. a video stream captured by an endoscope, and/or a video stream captured another camera or microscope (such as those used in open surgery)) and/or other information to aid the operator (e.g. surgeon) in performing the surgery. The display may be two-dimensional (2D) or three-dimensional (3D).

A control system 128 converts the movement of (and actions performed on/via) the input devices into control signals to move the arm joints and/or instrument end effector of the surgical robot. In some cases, the control system 128 is configured to generate control signals to move the arm joints and/or instrument end effector based on the position in space of the input devices and their orientation.

Although the example surgical robot system of FIG. 1 comprises a single surgical robot, in other examples, a surgical robot system may comprise a plurality of surgical robots. For example, FIG. 2 illustrates a surgical robot system 200 with multiple robots 202, 204, 206 operating in a common workspace on a patient 208.

As a surgical robot system 100, 200 is used to perform a surgical procedure on a patient it is important the component or elements of the system communicate with each other as expected and that the control system 128 issues accurate command to the surgical robot arm(s) in light of the state of the surgical robot arm(s) and the other components of the system, and the inputs received from the input devices. If the system is not operating as expected there can be severe, if not, catastrophic consequences. Accordingly, it may be desirable to implement one or more safety mechanisms which are able to determine if there is a fault with the surgical robot system, and the control system 128 in particular, and if a fault is detected, put the system, or one or more components of the system, into a safe state.

The embodiments described below are provided by way of example only and are not limiting of implementations which solve any or all of the disadvantages of known surgical robot system and/or method of controlling a surgical robot system.

SUMMARY

This summary is provided to introduce a selection of concepts that are further described below in the detailed description. This summary is not intended to identify key features or essential features of the claimed subject matter, nor is it intended to be used to limit the scope of the claimed subject matter.

Described herein are control system for controlling a surgical robot system, the surgical robot system comprising a surgical robot, the surgical robot comprising a base, and an arm extending from the base to an attachment for an instrument, the arm comprising a plurality of joints whereby the configuration of the arm can be altered. The control systems include: a main controller configured to: receive communications identifying inputs from an operator of the surgical robot; generate control signals for controlling the movement of the surgical robot arm based on the inputs; and send communications to the surgical robot identifying the control signals; and a safety device situated such that communications to and from the main controller pass through the safety device, the safety device being operable to selectively filter the communications to and/or from the main controller.

A first aspect provides a control system for controlling a surgical robot system, the surgical robot system comprising a surgical robot, the surgical robot comprising a base, and an arm extending from the base to an attachment for an instrument, the arm comprising a plurality of joints whereby the configuration of the arm can be altered, the control system comprising: a main controller configured to: receive communications identifying inputs from an operator of the surgical robot; generate control signals for controlling the movement of the surgical robot arm based on the inputs; and send communications to the surgical robot identifying the control signals; and a safety device situated such that communications to and from the main controller pass through the safety device, the safety device being operable to selectively filters the communications to and/or from the main controller.

The safety device may be configured to filter at least a portion of the communications to and/or from the main controller in response to the surgical robot system being in a fault state.

The safety device may comprise one or more filters, and the one or more filters are configured to filter the communications to and/or from the main controller by comparing received communications to one or more filter criteria.

The one or more filters may comprise a receive filter and the one or more filter criteria may comprise one or more receive filter criteria, the receive filter may be configurable to filter the communications from the main controller by comparing the communications from the main controller to the one or more received filter criteria.

The receive filter may comprise a buffer to store the communications received from the main controller.

The receive filter may comprise a manifold and one or more matchers, the manifold configured to extract relevant information from the received communications prior to storing the received communications in the buffer, and the one or more matchers are configured to compare the relevant information to the one or more receive filter criteria.

The one or more receive filter criteria may comprise up to N receive filter criteria, wherein N is an integer based on a number of comparisons that can be performed between a communication and a filter criteria in a cycle and a number of cycles it takes to receive a communication.

It may take up to X cycles to receive a communication and N may be selected such that a communication can be compared with N filter criteria within X cycles.

The one or more filter criteria may comprise one or more transmit filter criteria and the at least one filter comprises a transmit filter, the transmit filter may be configurable to filter the communications to the main controller by comparing the communications to the main controller to the one or more transmit filter criteria.

The transmit filter may comprise a buffer to store the communications to the main controller.

The transmit filter may comprise a manifold and one or more matchers, the manifold may be configured to extract relevant information from the communications to the main controller prior to storing the communications to the main controller in the buffer, and the one or more matchers may be configured to compare the relevant information to the one or more transmit filter criteria.

The one or more transmit filter criteria may comprises up to K receive filter criteria, wherein K is an integer based on a number of comparisons that can be performed between a communication and a filter criteria in a cycle and a number of cycles it takes to receive a communication.

It may take X cycles to receive a communication and K may be selected such that a communication can be compared with K filter criteria within X cycles.

The one or more filter criteria may be configurable.

The one or more filter criteria may be configurable to cause the safety device to filter all communications to and from the main controller.

The one or more filter criteria may be configurable to cause the safety device to filter communications between the main controller and a specific device in the surgical robot system.

Each of the one or more filter criteria may comprise one or more of a source address, destination address, source port and destination port.

The safety device may comprise one or more registers and each filter criteria may be stored in a set of the one more registers.

The one or more filters may be configured to, in response determining that a communication matches at least one of the one or more filter criteria, reject the communication.

The one or more filters may be configured to reject the communication by discarding the communication.

The one or more filters may be configured to reject the communication by corrupting the communication.

The one or more filters may be configured to corrupt the communication by altering an error detecting portion of the communication.

The control system may further comprise a safety monitor and the safety device may be configured to send a copy of at least a portion of the communications to and/or from the main controller to the safety monitor.

The safety monitor may be configured to analyse the received communications to determine whether the surgical robot system is in a fault state, and in response to determining that the surgical robot system is in a fault state, cause the safety device to filter at least a portion of the communications to and/or from the main controller.

A second aspect provides a method of selectively filtering communications to and/or from of a main controller of a surgical robot system, the surgical robot system comprising a surgical robot, the surgical robot comprising a base, and an arm extending from the base to an attachment for an instrument, the arm comprising a plurality of joints whereby the configuration of the arm can be altered, the main controller configured to receive communications identifying inputs from an operator of the surgical robot, generate control signals for controlling the movement of the surgical robot arm based on the inputs, and send communications to the surgical robot identifying the control signals, the method comprising: receiving at a safety device a communication to or from the main controller; determining whether at least one filter criteria has been specified; in response to determining that at least one filter criteria has been specified, comparing the received communication to the at least one specified filter criteria; in response to determining that the received communication matches at least one of the at least one filter criteria, rejecting the receiving communication; and in response to determining that the received communication does not match any of the at least one filter criteria, outputting the communication to the relevant device.

The above features may be combined as appropriate, as would be apparent to a skilled person, and may be combined with any of the aspects of the examples described herein.

BRIEF DESCRIPTION OF THE DRAWINGS

Examples will now be described in detail with reference to the accompanying drawings in which.

Figure 1:
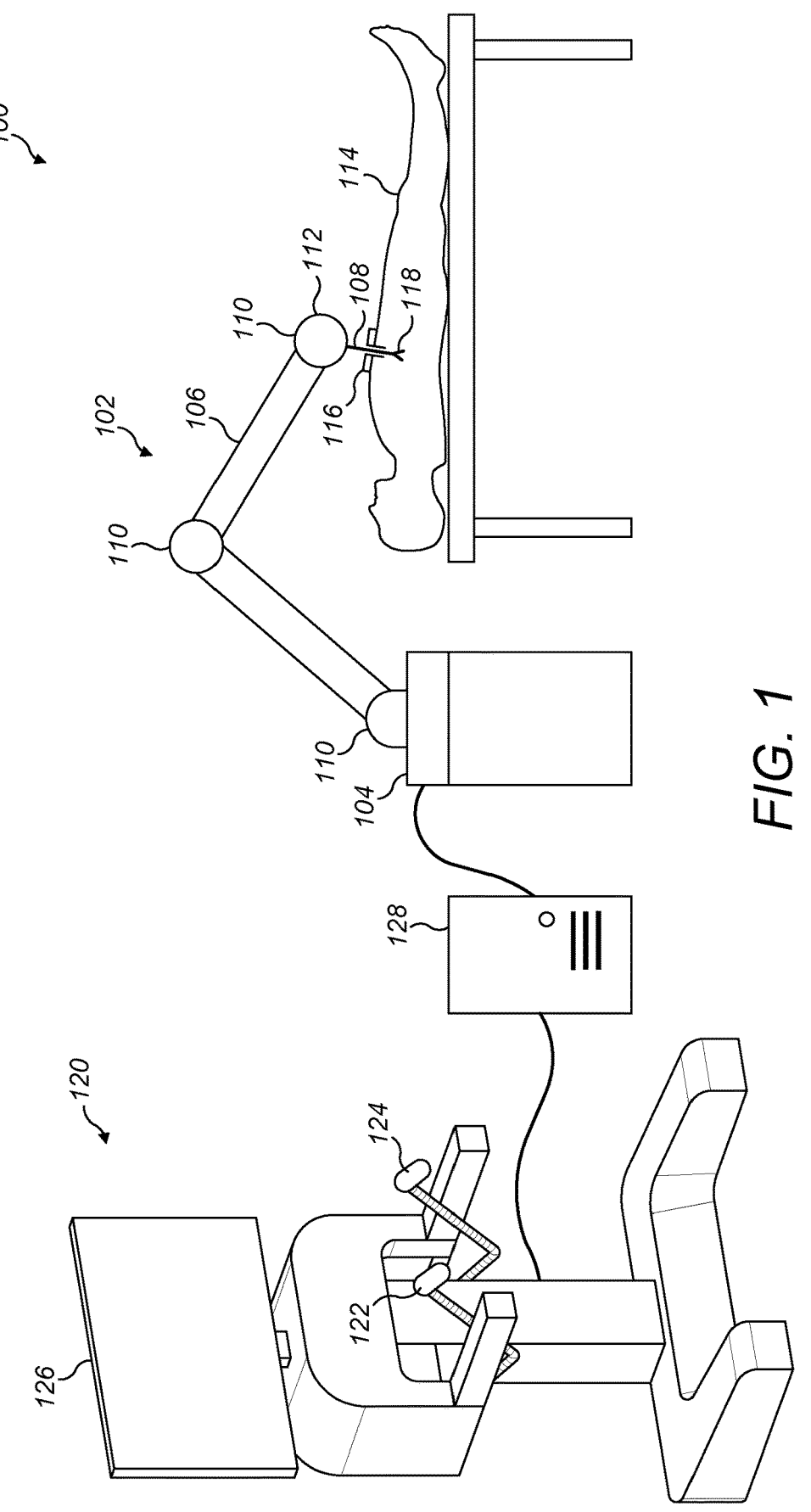
FIG. 1 is a schematic diagram of an example surgical robot system comprising a surgical robot, an operator console and a control system.
Figure 2:
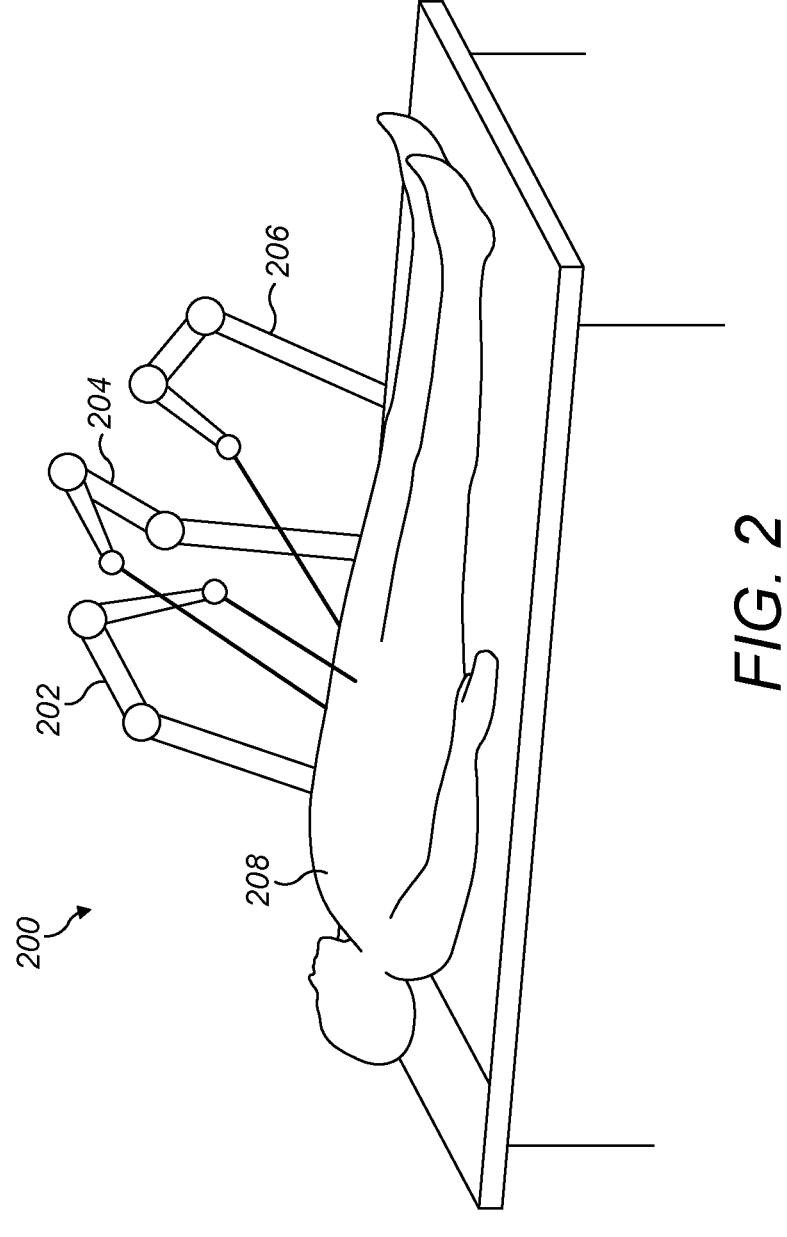
FIG. 2 is a schematic diagram of an example surgical robot system comprising a plurality of surgical robots.

The accompanying drawings illustrate various examples. The skilled person will appreciate that the illustrated element boundaries (e.g., boxes, groups of boxes, or other shapes) in the drawings represent one example of the boundaries. It may be that in some examples, one element may be designed as multiple elements or that multiple elements may be designed as one element. Common reference numerals are used throughout the figures, where appropriate, to indicate similar features.

DETAILED DESCRIPTION

The following description is presented by way of example to enable a person skilled in the art to make and use the invention. The present invention is not limited to the embodiments described herein and various modifications to the disclosed embodiments will be apparent to those skilled in the art. Embodiments are described by way of example only.

Described herein are control systems for surgical robot systems that comprise a remote operator console by which an operator can provide inputs, and a surgical robot arm comprising a series of joints extending from a base to a terminal end for attaching a surgical instrument. The control systems comprise a main controller and a safety device. The main controller is configured to receive communications from the operator console identifying operator inputs, convert those operator inputs to control commands to control the movement of the surgical robot, and send communications to the surgical robot arm that identify the control commands. The safety device is situated between the main controller and other components of the system such that the communications to and from the main controller pass through the safety device. The safety device is operable to selectively filter communications to and/or from the main controller. The safety device may be configured to filter at least a portion of the communications to/from the main controller response to the safety device itself, or another device, detecting that the surgical robot system in a fault state. A fault state may be that the main controller or another device in the system is not acting as expected.

In some cases, the control system may further comprise a safety monitor which is configured to verify the operation of the main controller and/or one or more other components of the system. In these cases, the safety device may be configured to send a copy of, at least a portion, of the communications to and from the main controller to the safety monitor, and the safety monitor may analyse the received communications to verify that the main controller and/or one or more other components is/are operating as expected. In response to detecting that the main controller and/or one or more other components of the system is not operating as expected, the safety monitor may cause the safety device to filter at least a portion of the communications to and from the main controller.

Figure 3:
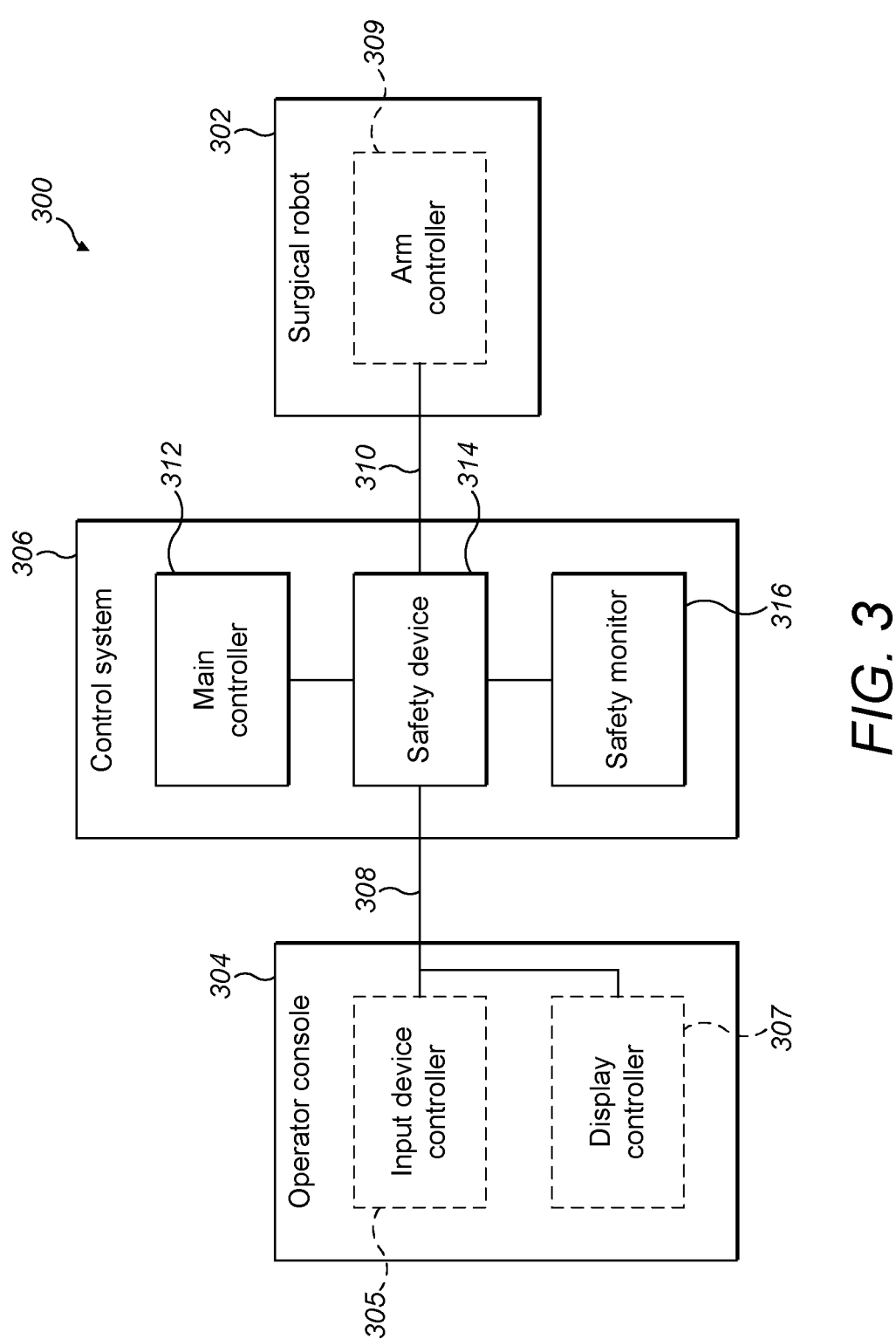
FIG. 3 is a block diagram of an example control system for a surgical robot system.

Reference is now made to FIG. 3 which illustrates an example surgical robot system 300. The surgical robot system 300 comprise a surgical robot 302; an operator console 304 for providing operator inputs for controlling the surgical robot 302; and a control system 306 for driving the surgical robot 302 in accordance with the operator inputs. The surgical robot 302 comprises a base and an arm extending from the base to an attachment for an instrument. The arm comprises a plurality of joints whereby the configuration of the arm can be altered. An example surgical robot which may be used to implement the surgical robot 302 of FIG. 3 is described below with respect to FIG. 5.

The operator console 304 may be located in the same room (e.g. operating theatre) as the surgical robot 302 or remotely from it. The operator console 304 allows the operator to provide input commands to the control system 306 to control the movement of the surgical robot 302. The operator console 304 may comprise input devices for controlling the state of the surgical robot arm and/or the instrument attached thereto. The input devices may be, for example, handgrips or hand controllers (e.g. one for each hand), with one or more buttons thereon, mounted on parallelogram linkages. Each input device may comprise an input device controller 305 that is configured to transmit the inputs received via the input device to the control system 306. The operator console 304 may also comprise a display. The display is used to display a video stream of the surgical site (e.g. a video stream captured by an endoscope, and/or a video stream captured another camera or microscope (such as those used in open surgery)) and/or other information to aid the operator (e.g. surgeon) in performing the surgery. The display may comprise a display controller 307 that is configured to receive display information from the control system 306 and provide inputs related thereto to the control system 306. An example operator console, which may be used to implement the operator console 304 of FIG. 3, was described above with respect to FIG. 1.

The control system 306 is coupled to the operator console 304 (e.g. the input device controller(s) 305 and the display controller 307 thereof) via one or more communications links 308 and receives communications from the operator console 304 (e.g. the input device controller(s) 305 and the display controller 307 thereof) identifying operator inputs via the one or more communications links 308. The operator inputs may be generated by the input devices (e.g. hand controllers) and/or other components of the operator console such as a foot pedal(s) inputs, voice recognition system, gesture recognition system, eye recognition system etc. The control system 306 is also coupled to the surgical robot 302 (e.g. an arm controller 309 thereof, which may also be referred to as an arm base controller (ABC)) via one or more communications links 310. The control system 306 may receive communications from the surgical robot 302 identifying the state or status of the surgical robot 302 via the one or more communications links 310. The state of the surgical robot 302 may, for example, be identified by one or more of: sensor data from position sensors and/or torque sensors located on the robot arm joints, force feedback data, and data from or about the surgical instrument attached thereto.

The control system 306 is configured to cause the surgical robot 302, and the instrument attached thereto, to move in response to the operator inputs it receives from the operator console 304 and the surgical robot state data received from the surgical robot 302. The control system 306 comprises a main controller 312 that is configured to: receive communications from the operator console 304 identifying the operator inputs and communications from the surgical robot 302 comprising surgical robot state data; generate control signals from the operator inputs and the surgical robot status data which cause the surgical robot, and/or any instrument attached there to move; and send communications to the surgical robot identifying the command signals. In other words, the main controller 312 is responsible for causing the surgical robot, and any instrument attached thereto to move in accordance with the user inputs. In the example described herein the main controller 312 is configured to receive inputs from the operator console 304 and generate a desired robot wrist position therefrom, and the desired position of drive elements to cause an instrument end effector to achieve a desired yaw, pitch and/or spread. The desired wrist pose and the drive element positions are then provided to the surgical robot arm (e.g. a surgical robot arm controller). As described in more detail below, the surgical robot arm (e.g. an arm controller thereof) may then determine the joint positions to achieve the desired wrist pose based on the joint information received form the torque and/or position sensors, and issue commands to individual joint controllers to move to the desired joint positions. However, this is an example only, and that in other surgical robot system the main controller 312 may perform different and/or additional functions.

For example, in some cases, the main controller 312 may perform one or more additional functions. For example, in some cases the main controller 312 may also be configured to provide and/or control at least part of a graphical user interface provided to the operator for providing input. The main controller 312 may comprise one or more processors (not shown) and a memory (not shown). The memory stores, in a non-transient way, software code that can be executed by the one or more processors to generate control signals for the surgical robot 302 and, optionally perform one or more additional functions.

In the example of FIG. 3 the control system 306 also comprises a safety device 314, and, optionally, a safety monitor 316. The safety device 314, which may also be referred to as the core safety supervisor (CSS), is a hardware device situated between the main controller 312 and the other components 302, 304 of the surgical robot system 300 such that communications to and from the main controller 312 pass through the safety device 314. Since the communications to and from the main controller 312 pass though the safety device 314, the safety device 314 can control the communications to and from the main controller 312. Specifically, the safety device 314 can prevent communications between the main controller 312 and one or more of the components 302, 304 (or parts or components thereof) when it has been detected that the surgical robot system 300 is in a fault state. In some cases, the components or devices in the system that communicate with the main controller 312 may be configured to: receive communications from the main controller at a predetermined interval or frequency, and automatically transition into a safe state if they cease to receive such communications for a period of time (e.g. a predetermined number of intervals). Accordingly, cutting off communication between the main controller and a component or device may automatically cause that component or device to transition to a safe state.

In some cases, the safety device 314 may be operable to selectively filter the communications to and/or from the main controller 312 based on one or more filter criteria. In some cases, the safety device 314 may comprise one or more programmable filters which can be programmed or configured to filter certain communications to and/or from the main controller 312. In some cases, the filters may be programmed to: filter none of the communication to and from the main controller 312; filter all communications to and from the main controller 312 (i.e. to cut off communications between the main controller 312 and the other components and devices of the system); and/or filter communications between the main controller 312 and one or more specific components or devices (e.g. between the main controller 312 and the operator console 304 or a part thereof, or between the main controller 312 and the surgical robot 302 or a part of thereof). As described in more detail below, where the components and devices in the surgical robot system 300 communicate with the main controller 312 using TCP/IP packets, the one or more filters may be configurable to filter communications based on IP source, IP destination address, source UDP port and/or destination UDP port.

In some cases, the safety device 314 may be configured to filter at least a portion of the communications to and/or from the main controller in response to it being detected that the surgical robot system 300 is in a fault state. The surgical robot system 300 may be deemed to be in a fault state if, for example, the main controller 312 is sending control signals to the surgical robot 302 that are not consistent with the state of the surgical robot 302. Further examples of surgical robot system 300 fault states which may be detected are described below. In some cases, the safety device 314 itself may be configured to detect when the surgical robot system 300 is in a fault state. In other cases, another device, such as the safety monitor 316 (described below) may also, or alternatively, be configured to detect when the surgical robot system 300, is in a fault state.

In some cases, the main controller 312 may be implemented using a field-programmable gate array (FPGA). However, it will be evident to a person of skill in the art that this is an example only. An example implementation of the safety device 314 is described below with respect to FIG. 5.

In some cases, as shown in FIG. 3, the control system 306 may also comprise a safety monitor 316, which may also be referred to as a core safety monitor (CSM). The safety monitor 316 is configured to independently verify the operation of the main controller 312, and/or one or more other components and devices in the system, by monitoring the communications to and from the main controller 312. In these cases, the safety device 314 may be configured to send a copy of, at least a portion, of the communications to and/or from the main controller 312 to the safety monitor 316. The safety monitor 316 is then configured to analyse the received communications to determine if the surgical robot system 300 is in a fault state. If the safety monitor 316 detects that the surgical robot system 300 is in a fault state, the safety monitor 316 may be configured to cause the safety device 314 to filter at least a portion of the communications to and/or from the main controller 312. An example implementation of the safety monitor 316 is described below with reference to FIG. 8.

The communications links 308, 310 between the control system 306 and the other components (e.g. operator console 304 and surgical robot 302) may be any suitable communications links that enables data communications between the control system 306 and the component. The communications links 308, 310 may all be of the same type, or at least two of the communications links 308, 310 may be of different types. Examples of suitable communications links include, but are not limited to, a wired communications link (e.g. an Ethernet, Token Ring, or RS232 link), or a wireless communications link (e.g. a Wi-Fi, Bluetooth, Bluetooth LE, or NFC link).

While the example surgical robot system 300 of FIG. 3 comprises a single surgical robot 302 with a single arm, it will be evident to a person of skill in the art that this is an example only and that the methods and techniques described herein are equally applicable to surgical robot systems with more than one surgical robot or surgical robots with more than one arm.

While the example control system 306 of FIG. 3 comprises a safety device 314 and a safety monitor 316, in other examples the control system 306 may only comprise a safety device 314, or may only comprise a safety monitor 316.

In some cases, the control system may physically form part of the operator console 304. In some cases, the main controller 312, safety device 314 and safety monitor 316 may be on a single printed circuit board (PCB).

Surgical Robot

Figure 4:
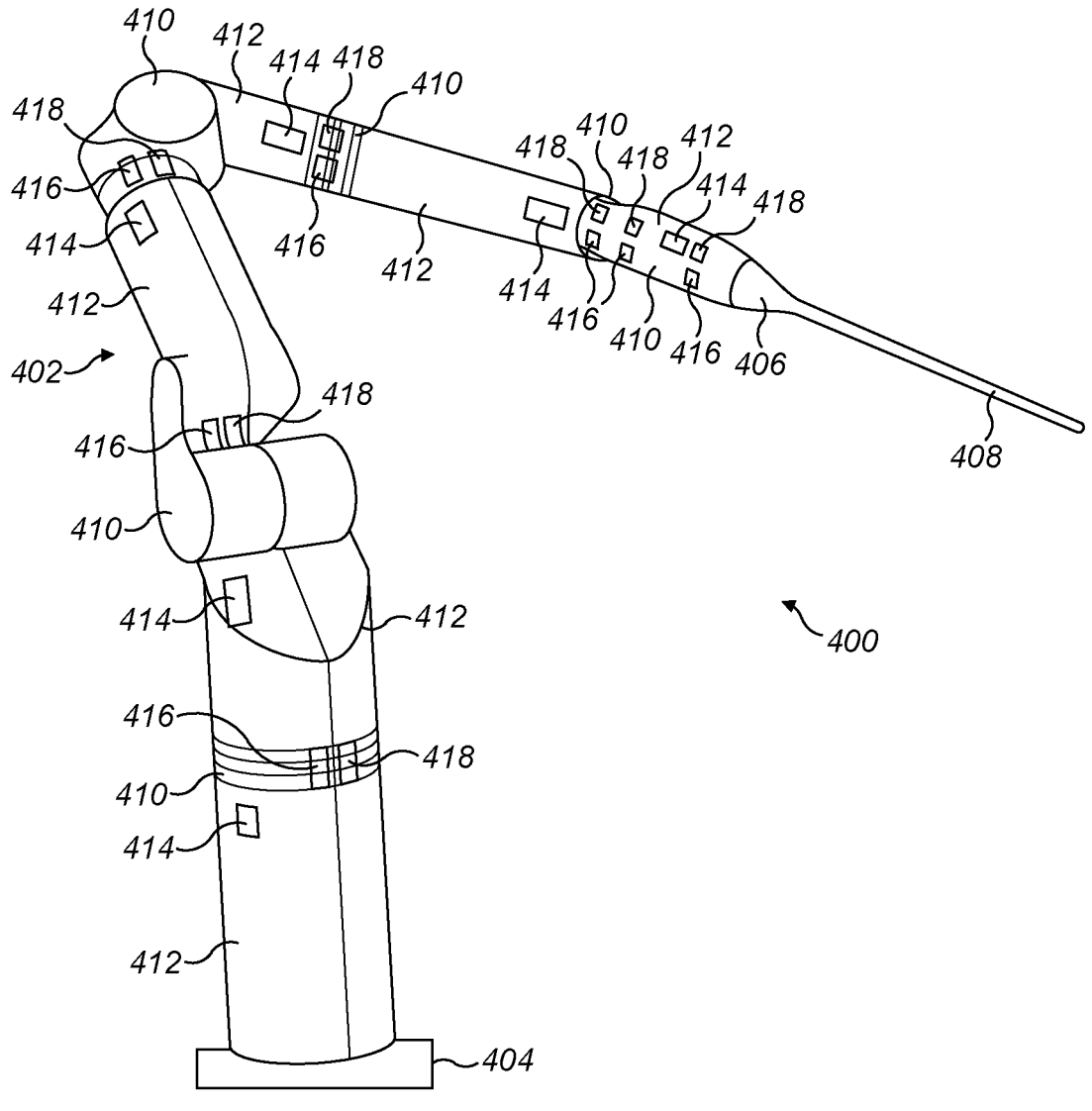
FIG. 4 is a schematic diagram of an example surgical robot arm.

Reference is now made to FIG. 4 which illustrates an example surgical robot 400 which may be used to implement the surgical robot 302 of FIG. 3. The surgical robot 400 comprises an arm 402 which extends from a base 404 which is fixed in place when a surgical procedure is being performed. In some cases, the base 404 may be mounted to a chassis. The chassis may be a cart, for example a bedside cart for mounting the robot at bed height. Alternatively, the chassis may be a ceiling mounted device, or a bed mounted device.

The arm 402 extends from the base 404 of the robot to an attachment 406 for a surgical instrument 408. The arm is flexible. It is articulated by means of multiple flexible joints 410 along its length. In between the joints are rigid arm members 412. The arm in FIG. 4 has seven joints. The joints include one or more roll joints (which have an axis of rotation along the longitudinal direction of the arm members on either side of the joint), one or more pitch joints (which have an axis of rotation transverse to the longitudinal direction of the preceding arm member), and one or more yaw joints (which also have an axis of rotation transverse to the longitudinal direction of the preceding arm member and also transverse to the rotation axis of a co-located pitch joint). However, the arm could be jointed differently. For example, the arm may have fewer or more joints. The arm may include joints that permit motion other than rotation between respective sides of the joint, for example a telescopic joint. The robot comprises a set of drivers 414, each driver 414 drives one or more of the joints 410.

The attachment 406 enables the surgical instrument 408 to be releasably attached to the distal end of the arm. The surgical instrument 408 has a linear rigid shaft and a working tip at the distal end of the shaft. The working tip comprises an end effector for engaging in a medical procedure. The surgical instrument may be configured to extend linearly parallel with the rotation axis of the terminal joint of the arm. For example, the surgical instrument may extend along an axis coincident with the rotation axis of the terminal joint of the arm. The surgical instrument 408 could be, for example, a cutting device, a grasping device, a cauterising device or image capture device (e.g. endoscope).

The robot arm comprises a series of sensors 416, 418. These sensors comprise, for each joint, a position sensor 416 for sensing the position of the joint, and a torque sensor 418 for sensing the applied torque about the joint's rotation axis. One or both of the position and torque sensors for a joint may be integrated with the motor for that joint.

Safety Device

Figure 5:
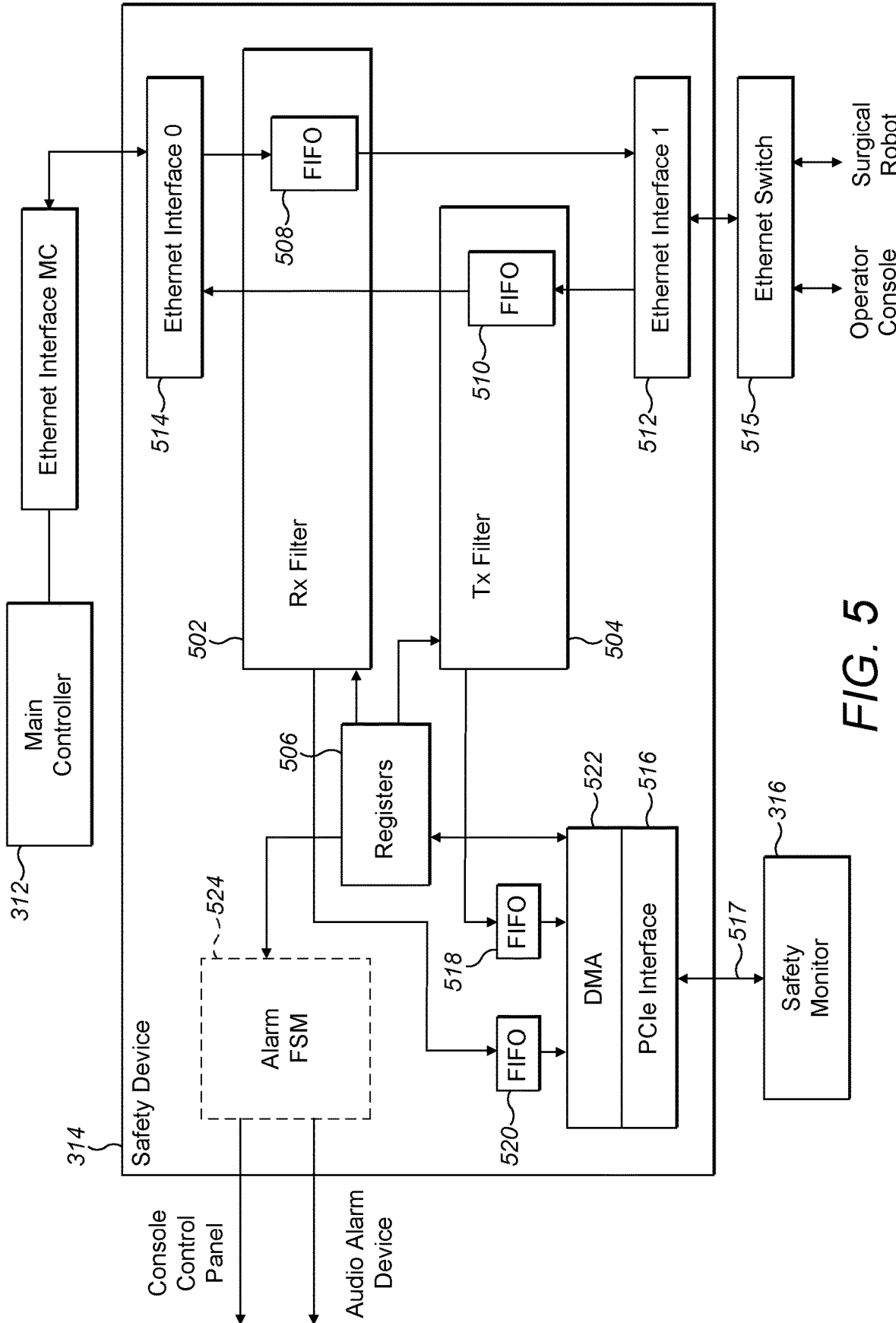
FIG. 5 is a block diagram of an example implementation of the safety device of FIG. 3 which comprises Tx and Rx filters.

Reference is now made to FIG. 5 which illustrates an example implementation of the safety device 314 of FIG. 3. As described above, the safety device 314 is situated between the main controller 312 and the other components of the surgical robot system 300 such that communications to and/or from the main controller 312 pass through the safety device 314. The safety device 314 is operable to selectively filter the communications to and/or from the main controller 312.

In the example, of FIG. 5 the safety device 314 comprises a receive (Rx) filter 502 and a transmit (Tx) filter 504 which are programmable filters which can be configured to selectively filter communications from and to the main controller 312, respectively. Where the main controller 312 uses UDP to communicate with the other components in the surgical robot system 300, the Rx and Tx filters may be configured to filter UDP packets. However, it will be evident to a person of skill in the art that this is an example only.

The Rx filter 502 receives communications from the main controller 312, and either: passes all communications to the other components if no Rx filter criteria are specified, or filters the communications in accordance with one or more specified Rx filter criteria. The Rx filter criteria specify the rules for selecting which communications to filter, reject or disallow to pass through the safety device 314. In some cases, the one or more Rx filter criteria may specify that all communications from the main controller 312 are to be filtered, or the one or more Rx filter criteria may specify that only communications matching specified criteria (e.g. a source/destination IP address, a source/destination UDP port or combination thereof) are to be filtered. When the Rx filter criteria specifies that all communications from the main controller 312 are to be filtered, the Rx filter 502 may simply reject all communications it receives. When, however, the Rx filter criteria specify that only communications matching specified criteria are to be filtered, the Rx filter 502 may be configured to compare each received communication against the specified criteria to determine if there is a match. Specifically, in some cases the Rx filter 502 may be configured to compare each communication (e.g. packet) with up to N different Rx filter criteria wherein N is an integer greater than or equal to one. As described in more detail below, N may be selected based on the number of comparisons that can be performed each cycle and the number of cycles it takes to receive a communication (e.g. packet).

The Rx filter criteria is configurable. For example, in some cases, as shown in FIG. 5, the safety device 314 may comprise a set of registers 506 which specify the Rx filter criteria. For example, where the main controller 312 uses UDP to communicate with the other components in the surgical robot system 300, the Rx filter 502 may be able to filter communications (e.g. packets) based on one or more of source IP address, destination IP address, source UDP port, and destination UDP port. In these cases, the set of registers 506 may comprise a register that indicates whether or not all communications are to be filtered; and one or more registers for each possible comparison that indicates which combination of source IP address, destination IP address, source UDP port and destination port that is to be compared against each communication (e.g. packet); and identifies the source IP address, destination IP address, source UDP port and/or destination UDP port to be used for the comparison. For example, Table 1 illustrates an example set of four 32-bit registers which can be used to specify a combination of source IP address, destination IP address, source UDP port and destination UDP port to be compared against each communication (e.g. packet). The set of registers 506 may comprise four registers for each of the N comparisons that the Rx filter can perform on each communication (e.g. packet).

TABLE 1

| Register | Bit(s) | Purpose |
|---|---|---|
| 1 | [0] | Match enabled - indicates whether a comparison should be performed |
| 1 | [4] | Destination port enable - indicates whether the destination UDP port of the packet should be compared to the destination port specified below |
| 1 | [5] | Source port enable - indicates whether the source UDP port of the packet should be compared to the destination port specified below |
| 1 | [6] | Destination address enable - indicates whether the destination IP address of the packet should be compared to the destination IP address specified below |
| 1 | [7] | Source address enable - indicates whether the source IP address of the packet should be compared to the source IP address specified below |
| 2 | [15:0] | Destination Port - the destination UDP port to be compared against the destination port of the packet |
| 2 | [31:16] | Source Port - the source UDP port to be compared against the source port of the packet |
| 3 | [31:0] | Destination IP Address - the destination IP address to be compared against the destination IP address of the packet |
| 4 | [31:0] | Source IP Address - the source IP address to be compared against the source IP address of the packet |

In some case, as shown in FIG. 5, the Rx filter 502 may comprises a buffer 508, such as a first in first out (FIFO) queue, which is used to store received communications before they are forwarded to the main controller 312. As described in more detail below with respect to FIG. 6, a complete communication (e.g. packet) may be received over several cycles (e.g. clock cycles). So as to not introduce any latency in re-transmitting the communications to the other components or devices, the Rx filter 502 may be configured to complete its filter determination by the time the complete communication has been received. For example, if it takes 8 cycles to receive a communication then the Rx filter 502 may be configured to determine whether the communication is to be filtered within 8 cycles.

When the Rx filter 502 identifies a communication (e.g. packet) that is to be filtered out (i.e. any communication if all communications to the main controller 312 are to be filtered, or a communication that matches the specified filter criteria otherwise) the Rx filter 502 is configured to reject that communication. In some cases, the Rx filter 502 may reject a communication by discarding the communication— i.e. not outputting or forwarding the communication to the appropriate device. However, in other cases, the Rx filter 502 may be configured to reject a communication by invalidating or corrupting the communication. In some cases, the Rx filter 502 may be configured to invalidate or corrupt a communication by altering an error detecting portion of the communication, such as, but not limited to a cyclic redundancy check (CRC) portion of the communication. Invalidating or corrupting the communication, as opposed to discarding the communication, may allow the filtering to be performed faster (e.g. in real time).

The Tx filter 504 operates in a similar manner as the Rx filter 502. Specifically, the Tx filter 504 receives communications directed, or addressed, to the main controller 312, and either: passes all communications to the main controller 312 if no Tx filter criteria are specified, or filters the communications in accordance with one or more specified Tx filter criteria. The Tx filter criteria specify the rules for selecting which communications to filter, reject, or disallow to pass through the safety device 314. In some cases, the one or more Tx filter criteria may specify that none of the communications to the main controller 312 are to be filtered, all communications to the main controller 312 are to be filtered, or only communications matching specified criteria (e.g. a source/destination IP address, a source/destination UDP port or combination thereof) are to be filtered. When no Tx filter criteria are specified, the Tx filter 504 may pass all communications it receives to the main controller 312. When the Tx filter criteria specifies that all communications to the main controller 312 are to be filtered, the Tx filter 504 may simply reject all communications it receives. When, however, the Tx filter criteria specifies that only communications matching specified criteria are to be filtered, the Tx filter 504 may be configured to compare each received communication against the specified criteria to determine if there is a match. Like the Rx filter 502, the Tx filter 504, may be configured to compare each communication (e.g. packet) with up to N different Tx filter criteria wherein N is an integer greater than or equal to one.

The Tx filter criteria, like the Rx filter criteria, is configurable. For example, the set of registers 506 may be used to specify which criteria, if any, are to be used to filter the communications to the main controller 312. For example, where the main controller 312 uses UDP to communicate with the other components and devices in the surgical robot system 300, the Tx filter 504 may be able to filter communications (e.g. packets) based on one or more of: source IP address, destination IP address, source UDP port, and destination UDP port. In these cases, the set of registers 506 may comprise a register that indicates whether of not all communications from the main controller 312 are to be filtered; and one or more registers for each comparison that indicates which combination of source IP address, destination IP address, source UDP port and destination port is to be compared against each communication (e.g. packet); and identifies the source IP address, destination IP address, source UDP port and/or destination UDP port to be used for the comparison. For example, Table 1 illustrates an example set of four 32 bits registers which can be used to specify a combination of source IP address, destination IP address, source UDP port and destination UDP port to be compared against each communication (e.g. packet). The set of registers 506 may comprise four registers for each of the N comparisons that the Tx filter 504 can perform on each communication (e.g. packet).

In some cases, as shown in FIG. 5, the Tx filter 504 may comprise a buffer (e.g. a first in first out (FIFO) queue) 510 which is used to store communications received from other components or devices in the system before they are forwarded to the main controller 312. As described in more detail below with respect to FIG. 6, a complete communication (e.g. packet) may be received over several cycles (e.g. clock cycles). So as to not introduce any latency in re-transmitting the communications to the main controller 312, the Tx filter 504 may be configured to complete its filter determination by the time the complete communication has been received. For example, if it takes 8 cycles to receive a communication, then the Tx filter 504 may be configured to determine whether the communication is to be filtered within 8 cycles.

When the Tx filter 504 identifies a communication (e.g. packet) that is to be filtered out (i.e. any communication if all communications to the main controller 312 are to be filtered, or a communication that matches the specified filter criteria otherwise) the Tx filter 504 is configured to reject that communication. In some cases, the Tx filter 504 may reject a communication by discarding the communication— i.e. not outputting or forwarding the communication to the appropriate component or device. However, in other cases the Tx filter 504 may be configured to reject a communica-tion by invalidating or corrupting the communication. In some cases the Tx filter 504 may be configured to invalidate or corrupt a communication by altering an error detecting portion of the communication, such as, but not limited to a cyclic redundancy check (CRC) portion of the communica-tion. Invalidating or corrupting the communication as opposed to discarding the communication may allow the filtering to be performed faster (e.g. in real time)

Example implementations of the transmit (Tx) and receive (Rx) filters 504, 502 of FIG. 5 are described below with respect to FIG. 6.

In some cases, the safety device 314 may receive com-munications from, and transmit communications to, other devices or components in the system via a first communi-cation interface 512; and may receive communications from, and transmit communications to the main controller 312, via a second communication interface 514. In the example shown in FIG. 5 the first and second communication inter-faces 512, 514 are Ethernet interfaces, however, it will be evident to a person of skill in the art that this is an example only and that in other examples different communication interfaces may be used and/or the first and second commu-nication interfaces 512, 514 may not be the same type of communication interface. In some cases, as shown in FIG. 5, the first communication interface 512 may be connected or coupled to a switch 515 (e.g. an Ethernet switch) by which it receives the communications from the other com-ponents and devices of the system. For example, the opera-tion console 304 and/or surgical robot 302 may be directly or indirectly connected to the switch 515.

Where the control system 306 also comprises a safety monitor 316, the receive (Rx) and transmit (Tx) filters 502, 504 may also be configured to forward a copy of, at least a portion of, the communications to and from the main con-troller to the safety monitor 316 to allow the safety monitor 316 check that the main controller 312 and/or one or more other components or devices in the surgical robot system 300 is/are operating as expected. In some cases, the Rx and Tx filters 502, 504 may be configured to forward all received communications between the main controller 312 and the other components/devices in the system to the safety moni-tor 316 regardless of whether the communication is filtered by the Rx or Tx filters 502, 504. However, in some cases, if a filter 502, 504 forwards a filtered communication to the safety monitor 316, the filter 502, 504 may notify the safety monitor 316 that the communication was filtered.

In some cases, as shown in FIG. 5, the safety device 314 may be configured to receive communications from and transmit communications to the safety monitor 316 over a separate communications link 517 (e.g. a PCIe link) via a safety monitor communication interface 516. In some cases, as shown in FIG. 5, the safety monitor communication interface 516 may be a different type of communication interface than the first and second communication interfaces 512, 514. For example, as shown in FIG. 5, the first and second communication interfaces 512, 514 may be Ethernet interfaces, whereas the safety monitor communication inter-face 516 may be a Peripheral Component Interconnect Express (PCIe) interface. In such cases, the communications to and/or from the main controller 312 which are to be forwarded to the safety monitor 316 may be encapsulated in another protocol so as to be provided to the safety monitor 316. In some cases, as shown in FIG. 5, the safety device 314 may comprise a set of buffers (e.g. FIFO queues) 518, 520 for storing a copy of the communications to and from the main controller 312 respectively to be forwarded to the safety monitor 316. As is known to those of skill in the art, a PCIe link is a high-speed which communications link or bus. Using a PCIe link can allow the copies of the commu-nication to and from the main controller 312 to be trans-ferred to the safety monitor 316 quickly and efficiently.

In addition to allowing data to be transferred quickly and efficiently, using a separate communications link 517 (e.g. PCIe link) to communicate with the safety monitor 316, instead of, for example, the common Ethernet network, allows the safety monitor 316 to be isolated from the remainder of the devices in the system. This can ensure that the other devices do not interfere with the operations of the safety monitor 316. Furthermore, using a separate commu-nications link between the safety device 314 and the safety monitor 316 allows the safety monitor 316 to snoop on the communications to and from the main controller 312, whereas if the safety monitor 316 were simply connected to the main (e.g. Ethernet) network the safety monitor 316 would only be able to read communications (e.g. packets) addressed to it.

As described above, the safety monitor 316 is configured to analyse the communications to and from the main con-troller 312 to determine whether the surgical robot system 300 is in a fault state. For example, the safety monitor 316 may be configured to determine that the surgical robot system 300 is in a fault state if the communications from the main controller indicate that a surgical robot arm is linked to a hand controller other than the hand controller shown as being linked to that surgical robot arm on the operator console display. An example implementation of the safety monitor 316 and example fault states that the safety monitor 316 may detect are described below with respect to FIGS. 8-10.

In some cases, if the safety monitor 316 detects that the surgical robot system 300 is in a fault state, the safety monitor 316 may be configured to cause the safety device 314 to filter all, or a portion of, the communications to and from the main controller 312. Depending on the type of fault that is detected, the safety monitor 316 may cause the safety device 314 to filter all communications to and/or from the main controller 312; or filter only a portion of the commu-nications to and/or from the main controller 312 (e.g. the communications between the main controller 312 and one or more devices/components). For example, if the fault state is one which can affect all parts of the system, the safety monitor 316 may be configured to cause the safety device 314 to filter all communications to and from the main controller 312. In some cases, each device or component that is in communication with the main controller 312 may be configured to transition into a safe state if it does not receive regular communications (e.g. heartbeat communications) from the main controller 312. In these cases, filtering all communications between to and from the main controller 312 may cause all the other devices in communication with the main controller 312 to transition to a safe state. In contrast, if the fault appears to be related to a particular device (e.g. one particular robot arm of a plurality of robot arms), the safety monitor 316 may be configured to cause the safety device 314 to filter only communications between the main controller 312 and that particular device.

In some cases, the safety monitor 316 may be configured to cause the safety device 314 to filter all, or a portion, of the communications to and from the main controller by writing to the registers 506 of the safety device 314 that specify the filter criteria.

In some cases, as shown in FIG. 5, to allow the high throughput data transfer(s) between the safety device and safety monitor 316 to occur efficiently, the safety device 314 may comprise a direct memory access (DMA) 522 between the safety monitor communication interface 516, and the buffer (e.g. FIFO queues) 518, 520 and the registers 506. As is known to those of skill in the art, a DMA is a device that allows an input/output (I/O) device to send or receive data directly to or from a storage unit, such as, memory or a buffer, bypassing the main processor. A DMA allows a main processor to perform other functions while a data transfer is being performed. In this example, the DMA allows data to be transferred between the safety device 314 and the safety monitor 316 with minimal interaction from either the safety device 314 or the safety monitor 316.

In the example of FIG. 5 it is the safety monitor 316 that is configured to identify that the surgical robot system 300 is in fault state; cause the safety device 314 to filter, at least a portion of, the communications to and from the main controller 312; and specify the filter criteria. However, in other examples, there may additionally or alternatively be one or more other components in the surgical robot system 300 that are configured to detect that the surgical robot system 300 is in a fault state and cause the safety device 314 to filter all or a portion of the communications to and/or from the main controller; and/or additionally or alternatively the safety device 314 itself may be able to detect that the surgical robot system 300 is in a fault state which may trigger the safety device 314 to filter all or a portion of the communications to and/or from the main controller.

In some cases, as shown in FIG. 5, the safety device 314 may also comprise an alarm finite state machine (FSM) 524 which is used to trigger alarms in the system, such as, but not limited to, audio alarms and/or visual alarms. For example, in some cases, the alarm FSM 524 may be connected to an audio alarm device which can be used to emit an audible alarm and/or a control panel of the console which can be used to display a visual alarm. In some cases, the alarm FSM may be controlled by the configuration of one or more registers in the set of register 506. Specifically, in some cases, writing a value or set of values to certain register(s) in the set of register 506 may cause the alarm FSM 524 to trigger a first type of alarm, and writing a different value or set of values to different register(s) in the set of registers may cause the alarm FSM 524 to trigger as second type of alarm.

In some cases, the safety monitor 316 may be able to control the alarm FSM 524, and thus the alarms that are triggered by the safety device 524, by, for example, writing to the appropriate registers in the set of registers 506.

Figure 6:
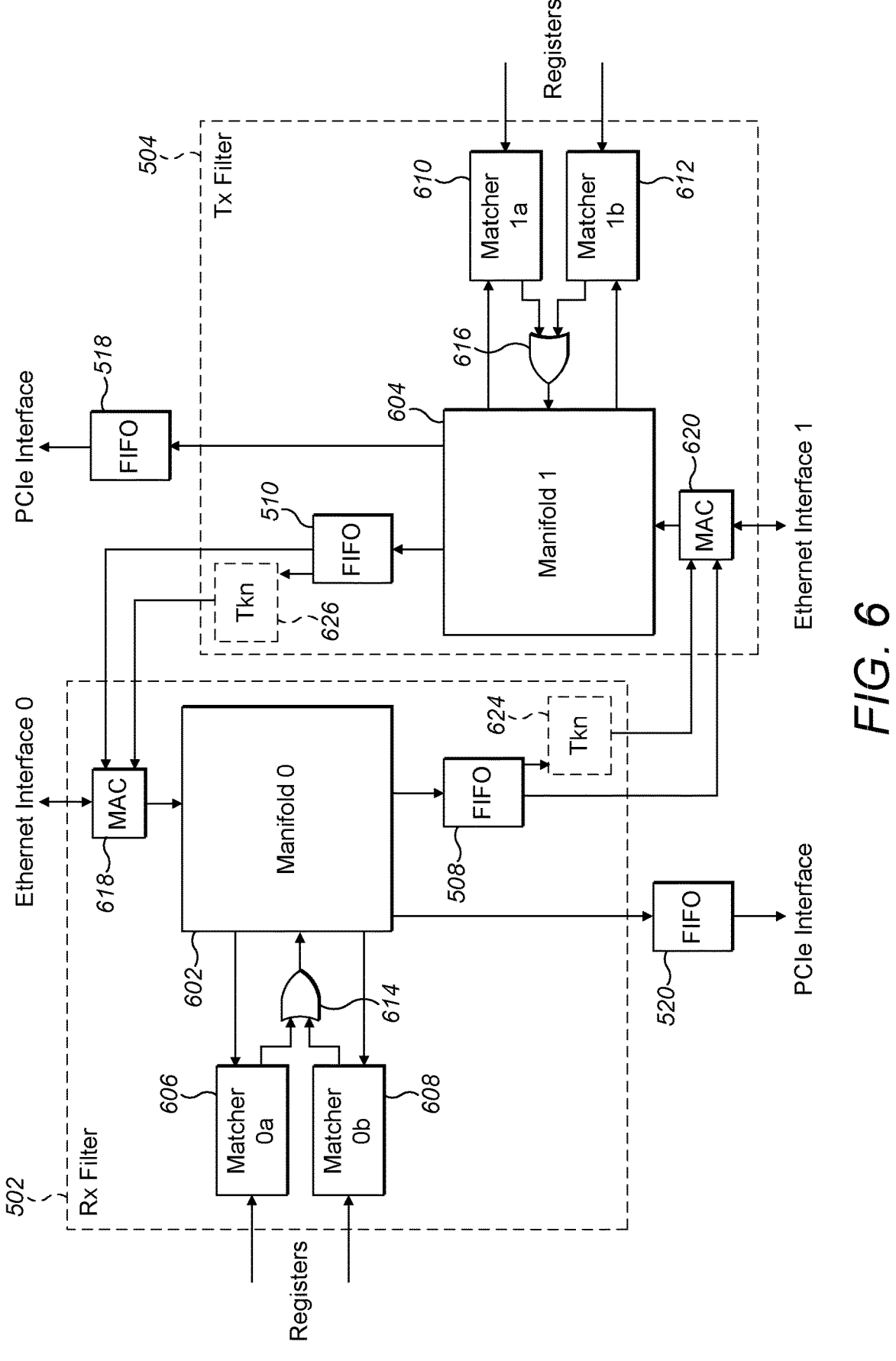
FIG. 6 is a block diagram of an example implementation of the Tx and Rx filters of FIG. 5.

Reference is now made to FIG. 6 which illustrates example implementations of the Rx and Tx filters 502, 504 of FIG. 5. In this example, each filter 502, 504 comprises a manifold 602, 604, one or more matchers 606, 608, 610, 612, combination logic 614, 616, a buffer (e.g. FIFO queue) 508, 510 and mac address control (MAC) logic 618, 620.

As known to those of skill in the art, MAC logic is responsible for the transmission of data packets to and from a communication interface. In this example, each MAC logic 618, 620 is configured to receive communications directed to the main controller 312, or communications from the main controller 312 from a communication interface, and provide the received communications to the corresponding manifold 602, 604. Specifically, the MAC logic 618 of the Rx filter 502 is configured to receive communications from the main controller 312 via the second communication interface 514) (e.g. Ethernet Interface 0) and forward the received communications to the first manifold 602. Similarly, the manifold 604 of the Tx filter 504 is configured to receive communications from other components or devices in the surgical robot system 300 that are directed to the main controller 312 via the first communication interface 512 (e.g. Ethernet Interface 1) and forward the received communications to the second manifold 604.

Each manifold 602, 604 is configured to store a copy of each received communication in the corresponding buffer (e.g. FIFO queue) 508, 510. Specifically, the manifold 602 of the Rx filter 502 is configured to receive communications from the main controller 312 and store a copy of each received communication in the buffer (e.g. FIFO queue) 508. The communications stored in the buffer (e.g. FIFO queue) 508 may (e.g. if they are not filtered) be subsequently forwarded to another component or device. Similarly, the manifold 604 of the Tx filter 504 is configured to receive communications from other components or devices in the surgical robot system 300 that are directed to the main controller 312, and store a copy of each received communication in the buffer (e.g. FIFO queue) 510. The communications stored in the buffer (e.g. FIFO 510) may (e.g. if they are not filtered) be subsequently forwarded to the main controller 312.

Each manifold 602, 604 is also configured to extract information, from each received communication, that is relevant for filtering the communications, and provide the extracted information to the corresponding matcher(s) 606, 608, 610, 612. The information relevant for filtering is the information or data in a communication that is used to determine whether or not the communication is to be filtered. For example, in some cases, the main controller 312 may be configured to communicate via UDP and each communication (e.g. each UDP packet) may be filtered based on one or more of: source IP address, destination IP address, source UDP port and destination UDP port. In these cases, each manifold 602, 604 may be configured to extract the source IP address, the destination IP address, source UDP port and/or destination UDP destination from the header of each received UDP packet and provide that information to the corresponding matcher(s) 606, 608, 610, 612.

Each manifold 602, 604 is also configured to receive, from the corresponding matcher(s) 606 and 608, 610 and 612, information for each communication indicating whether that communication matches at least one of the filter criteria and thus should be rejected. If a manifold 602, 604 receives information from the corresponding matcher(s) 606 and 608, 610 and 612 indicating that a communication is to be rejected the manifold 602, 604 may mark or identify the communication in the buffer (e.g. FIFO queue) 508, 510 as being a rejected communication. In some cases, a manifold 602, 604 may store a token alongside each communication (or each part of a communication) stored in a buffer (e.g. FIFO queue) 508, 510. The token may identify whether the communication is to be rejected or not, and if a communication has multiple parts it may identify the part of the communication. For example, where a communication can be received in a single cycle then the token stored alongside a communication may simply indicate whether that communication is to be rejected or not. Where, however, the communication may be received over multiple cycles, a token may be stored alongside each part of a communication (e.g. the part received in each cycle). For example, the token may specify whether the part of the communication is the start of the communication (e.g. packet), whether the part of the communication is the middle part of the communication (e.g. packet), whether the part of the communication is the end part of the communication (e.g. packet) and that it is not rejected, or whether the part of the communication is the end part of the communication (e.g. packet) and it is to be rejected.

Where the control system 306 also comprises a safety monitor 316 then, as shown in FIG. 5, each manifold 602, 604 may also be configured to store a copy of each received communication in a safety monitor buffer (e.g. FIFO queue) 520, 518 for transmission to the safety monitor 316. Specifically, the manifold 602 of the Rx filter 502 may be configured to store a copy of each received communication from the main controller 312 (e.g. those communications received via the first communication interface) in a first safety monitor buffer (e.g. FIFO queue) 520. The communications stored in the first safety monitor buffer (e.g. FIFO queue) 520 may then be subsequently transmitted to the safety monitor 316 (e.g. via the safety monitor communication interface 516). Similarly, the manifold 604 of the Tx filter 504 may be configured to store a copy of each communication to the main controller 312 (e.g. those communications received via the second communication interface) in a second safety monitor buffer (e.g. FIFO queue) 518. The communications in the second safety monitor buffer (e.g. FIFO queue) 518 may then be subsequently transmitted to the safety monitor 316 (e.g. via the safety monitor communication interface 516).

Each matcher 606, 608, 610, 612 is configured to compare the information received from the manifold 602, 604 for each communication to filter criteria to determine if there is a match. As described above, the filter criteria used by a matcher 606, 608, 610, 612 may be identified by a set of registers 506. In some cases, each matcher 606, 608, 610, 612 may be able to compare the relevant information for a communication to a plurality of different sets of filter criteria. Where each communication may be filtered based on one or more of: source IP address, destination IP address, source UDP port and destination UDP port, each set of filter criteria may comprise any combination of a source IP address, destination IP address, source UDP port and destination UDP port. However, it will be evident to a person of skill in the art that this is an example only and that other criteria may be used to filter communications.

In some cases, a matcher 606, 608, 610, 612 may be able to perform multiple comparisons in a cycle (e.g. clock cycle). For example, a matcher 606, 608, 610, 612 may be able to compare the relevant information for a communication to two different sets of filter criteria in a cycle (e.g. clock cycle). However, in other cases, a matcher 606 may only be able to compare the relevant information for a communication to a single set of filter criteria in a cycle (e.g. clock cycle).

In some cases, it may take a single cycle (e.g. clock cycle) to receive a complete communication. However, in other cases, due to the limited amount of data that can be received each clock cycle, it may take multiple cycles (e.g. clock cycles) to receive a complete communication. In either case, it may be desirous to be able to determine whether a communication is to be rejected (e.g. matches any of the filter criteria) before the end of the communication as it allows the communication to be marked or identified as a rejected communication (and optionally the CRC to be modified or corrupted) before the entire communication is stored in the corresponding buffer (e.g. FIFO queue) 520, 518. This may be described as performing the filtering in real-time. For example, if it takes eight cycles to receive a complete communication then it may be desirable to perform all comparisons within eight cycles (e.g. clock cycles). This may limit the number of comparisons that can be performed for each communication.

Accordingly, in some cases, each filter 502, 504 may comprise multiple matchers 606, 608, 610, 612 so as to increase the number of comparisons that can be performed for each communication (e.g. packet). For example, in the example shown in FIG. 6 each filter 502 and 504 comprises two matchers 606 and 608, 610 and 612. Where it takes 8 cycles to receive a complete communication, and each matcher 606, 608, 610 and 612 can perform one comparison per cycle, this means that up to 16 comparisons can be performed for each communication. However, it will be evident to a person of skill in the art that this is an example only and that in other examples there may be more or fewer matchers 606, 608, 610, 612.

If a matcher 606, 608, 610, 612 determines that the received information matches at least one set of filter criteria the matcher 606, 608, 610, 612 may output information indicating that there was a match. In some cases, once a matcher 606, 608, 610, 612 has received a set of relevant information from the manifold the matcher 606, 608, 610, 612 may continue to output an indication of whether the matcher has found, up to that point, the relevant information to match a filter criteria.

Where, as in the example of FIG. 6, each filter 502, 504 comprises multiple matchers 606, 608, 610, 612 each filter 502, 504 may comprise combination logic 614, 616 which is configured to combine the outputs of the corresponding matchers 606 and 608, 610 and 612 so as to provide a single input to the corresponding manifold 602, 604 that indicates whether any of the matchers have identified a match for a communication. In FIG. 6, each combination logic 614, 616 is implemented as an OR gate, but it will be evident to a person of skill in the art that this is an example only, and the combination logic 614, 616 may be implemented in any suitable manner.

Each MAC logic 618, 620 is also configured to send all non-rejected communications in the buffer of the other filter to the main controller/another device via a communications link, and reject all of the communications stored in that buffer that are marked or identified as rejected. MAC logic 618, 620 may reject a communication by not outputting that communication, or by corrupting the communication (e.g. by corrupting an error code (e.g. a CRC code) in the communication) Specifically, the MAC logic 618 of the Rx filter 502 is configured to send all non-rejected communications in the buffer 510 of the Tx filter 504 to the main controller via the second communication interface (e.g. Ethernet Interface 0) and reject all of the communications stored in that buffer 510 that are marked or identified as rejected. Similarly, the MAC logic 620 of the Tx filter 504 is configured to send all non-rejected communications in the buffer 508 of the Rx filter 502 to another device via the first communication interface (e.g. Ethernet Interface 1) and reject all of the communications stored in that buffer 508 that are marked or identified as rejected.

Where the manifolds 602, 604 are configured to store a token alongside each communication and/or each part of a communication that indicates whether or not the communication is to be rejected, each filter 502, 504 may further comprise token (TKN) logic 622, 624 that is configured to analyse the token(s) associated with each communication, or each part thereof, to determine if a communication output from the buffer is to be rejected, and if a token indicates that a communication is to be rejected, cause the corresponding MAC logic 618, 622 to reject that communication.

Figure 7:
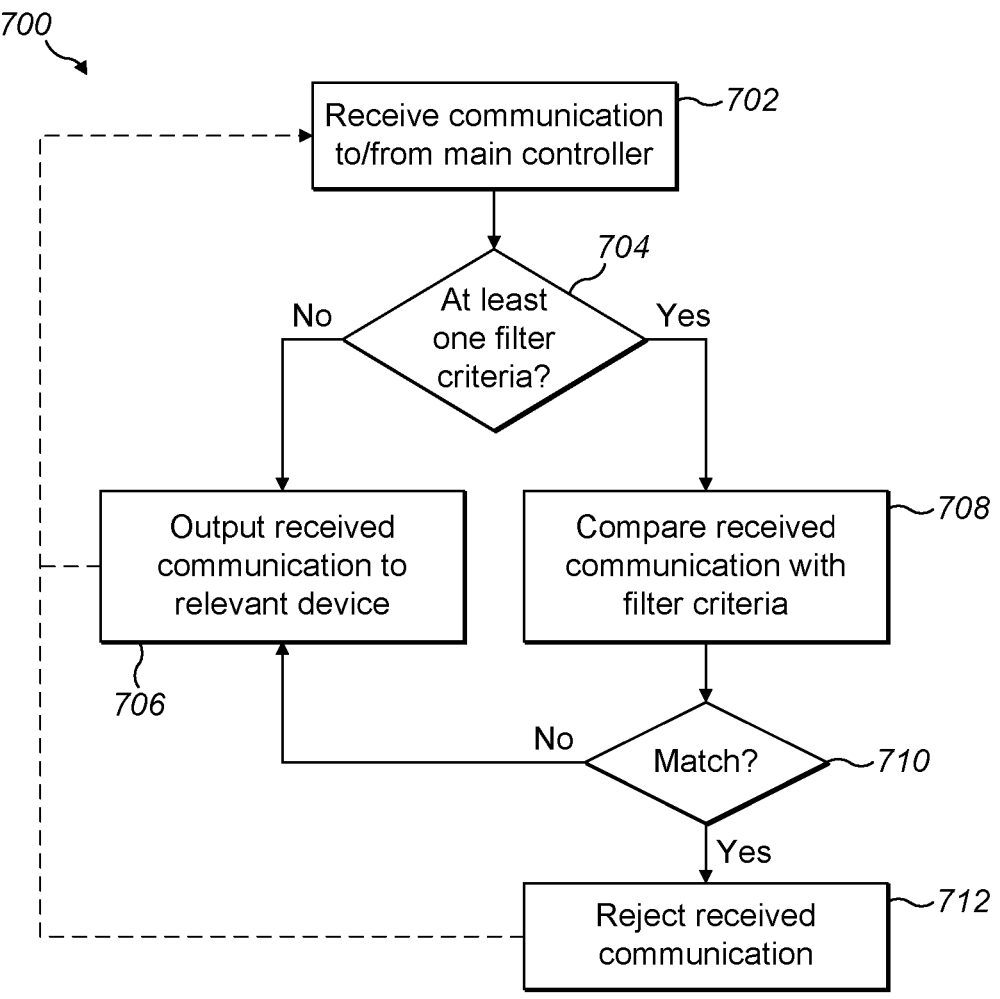
FIG. 7 is a flow diagram of an example method of selectively filtering communications to and/or from the main controller of FIG. 3, which may be implemented by the safety device of FIG. 3.

Reference is now made to FIG. 7 which illustrates an example method 700 of selectively filtering communications to and/or from the main controller 312, which may be implemented by the safety device 314 of FIG. 3. The method 700 begins at block 702 where the safety device 314 receives a communication to, or from, the main controller 312. The method 700 then proceeds to block 704 where the safety device 314 determines whether at least one filter criteria is specified. In some cases, the safety device 314 may determine whether at least one filter criteria is specified based on the configuration of one or more registers 506. If it is determined at block 704 that no filter criteria has been specified, then the method 700 proceeds to block 706. If, however, it is determined at block 704 that at least one filter criteria has been specified the method 700 proceeds to block 708.

At block 706, the safety device 314 outputs the received communication to the relevant device. For example, if the received communication is directed to the main controller 312 then the received communication may be output (e.g. via a communication interface or a communication connection) to the main controller 312. Similarly, if the received communication is from the main controller 312 then the received communication may be output (e.g. via a communication interface or a communications connection) to the appropriate device or component. Once the received communication has been output, the method 700 may end, or the method 700 may proceed back to block 702 where another communication to/from the main controller 312 is received.

At block 708, the safety device 314 compares the received communication against one or more filter criteria to determine if there is a match and thus the communication is to be rejected. Comparing the communication against one or more filter criteria may comprise extracting relevant information from the communication and comparing the relevant information to the filter criteria to determine if there is a match. The relevant information of a communication for filtering purposes may be based on the filtering criteria. For example, where each communication is a UDP packet that may be filtered based on one or more of: source IP address, destination IP address, source UDP port and destination UDP port, the relevant information for a communication (e.g. packet) is the source IP address, destination IP address, source UDP port and destination UDP port. It will be evident to a person of skill in the art that this is an example only, and that a communication may be filtered based on any data or information therein. Once the received communication has been compared to the filter criteria the method 700 proceeds to block 710.

At block 710, the safety device 314 determines if the received communication matches at least one filter criteria. If it is determined at block 710 that the communication matches at least one filter criteria, then the method 700 proceeds to block 712. If, however, it is determined at block 710 that the communication does not match any of the filter criteria, the method 700 proceeds to block 706 where the safety device 314 outputs the communication.

At block 712, after determining that the communication matches at least one filter criteria, the safety device 314 rejects the communication. In some cases, rejecting the communication may comprises discarding the communication (e.g. not outputting the communication). In other cases, rejecting the communication may comprise corrupting the communication, such that the communication will not be processed by the receiving device or component, prior to outputting the communication. In some cases, corrupting a communication may comprise corrupting an error code (e.g. a CRC code) in the communication. In some cases, an error code may be corrupted by setting it to all zeros. As described above, it may take more time to discard a communication than to corrupt a communication. Accordingly, corrupting communications as opposed to discarding communications may allow the filtering to be performed in real-time. In other words, corrupting communications that match the filter criteria may allow the filtering to be done without adding any (or only minimal) latency. Once the received communication has been rejected, the method 700 may end or the method 700 may proceed back to block 702 where another communication to, or from, the main controller 312 is received.

Safety Monitor

Figure 8:
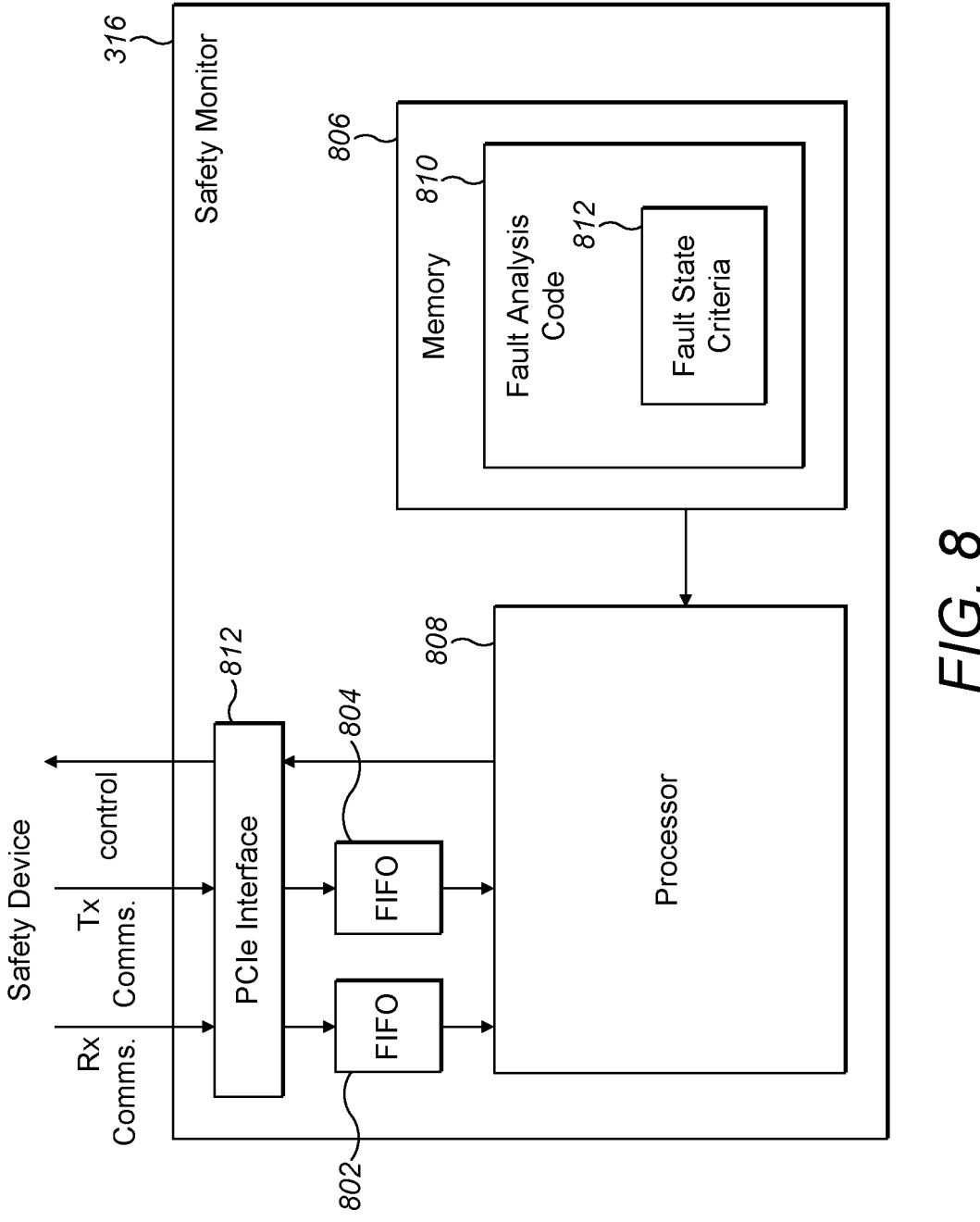
FIG. 8 is a block diagram of an example implementation of the safety monitor of FIG. 3.

Reference is now made to FIG. 8 which illustrates an example implementation of the safety monitor 316 of FIG. 3. The safety monitor 316 is a dedicated, and physically separate, component for monitoring the operation of the surgical robot system, and the main controller 312 in particular, based on the communications to and/or from the main controller 312. Specifically, the safety monitor 316 is configured to receive a copy of, at least a portion of, the communications to and/or from the main controller 312; analyse the communications to determine whether the surgical robot system 300 is in a fault state; and if it is determined that the surgical robot system is in a fault state, cause one or more devices in the system to transition to a safe state. In some cases, the safety monitor 316 may be configured to cause one or more devices or components in the system to transition to a safe state by causing the safety device 314 to filter at least a portion of the communications to and/or from the main controller 312.

In the example of FIG. 8 the safety monitor 316 comprises first and second buffers (e.g. FIFO queues) 802, 804 for storing the communications to and from the main controller 312 respectively; a memory 806; and a processor 808. Where the control system 306 comprises a safety device 314, the communications to and/or from the main controller 312 may be received from the safety device 314. The memory 806 is configured to store fault analysis code 810 which, when executed by the processor 808, causes the processor 808 to analyse the communications stored in the first and second buffers 802, 804 to determine if, based on one or more fault state criteria 812, the surgical robot system 300 is in a fault state; and in response to determining that the surgical robot system 300 is in a fault state, cause one or more devices in the surgical robot system 300 to transition to a safe state. The one or more devices which are transitioned to a safe state may be selected based on the type of fault state detected. For example, in some cases, only a single device in the surgical robot system 300 may be transitioned to a safe state, whereas, in other cases, more than one, or all of the devices in the surgical robot system 300 may be transitioned to a safe state.

As described above, in some cases, devices in the surgical robot system 300 that are in communication with the main controller 312 (e.g. an input device controller 305, a display controller 307 or an arm controller 309) may be configured to receive communications (e.g. a heartbeat communication or the like) from the main controller 312 at a predetermined interval or frequency, and if a device (e.g. an input device controller 305, a display controller 307 or an arm controller 309) doesn't receive such communications over a period of time (e.g. a predetermined number of intervals) the device may be configured to transition to a safe state. In some cases, a device may be said to be in a safe state when the device no longer has any control, or role, in the movement of any part of a surgical robot. When a device is in a safe state a patient cannot be harmed by the malfunctioning of the device. In these cases, the safety monitor 316 may be configured to cause a device to transition to a safe state by cutting off communications between the main controller 312 and that device.

Where, as shown in FIG. 3, the control system 306 comprises a safety device 314 which can be configured to filter communications to and/or from the main controller 312, the safety monitor 316 may be configured to cause a device to transition to a safe state by causing the safety device 314 to filter communications between the main controller 312 and that device. The safety monitor 316 may be configured to cause the safety device 314 to filter communications between the main controller and a specific device by sending control signals to the safety device 314 that adjust the one or more filter criteria so that such communications will be filtered. Where, as described with reference to FIG. 5, the safety monitor 316 comprises a set of registers 506 which specify the filter criteria to be used to filter communications, the safety device 314 may be configured to cause the safety device 314 to filter communications by writing data to the set of registers 506 to cause communications between the main controller 312 and the device to be filtered. Where, as described above with reference to FIG. 5, the set of registers 506 comprises a group of receive registers for each of a plurality of receive filter criteria and a group of transmit registers for each of a plurality of transmit filter criteria, the safety monitor 316 may be configured to: (i) identify a group of receive registers that is not currently in use, and configure the identified group of registers to indicate that the communications from the main controller are to be filtered based on source address and destination address, set the source address to the address of the main controller, and set the destination address to the address of the relevant device; and (ii) identify a group of transmit registers that is not currently in use, and configure the identified group of registers to indicate that communications to the main controller are to be filtered based on source address and destination address, set the source address to the address of the relevant device, and set the destination address to the address of the main controller 312.

In some cases, as shown in FIG. 8, the safety monitor 316 may receive the communications and/or send control signals through one or more communication interfaces 812. In the example shown in FIG. 8, the communication interface 812 is a PCIe interface, however, it will be evident to a person of skill in the art that this is an example only and that any suitable wired or wireless communication interface may be used.

Figure 9:
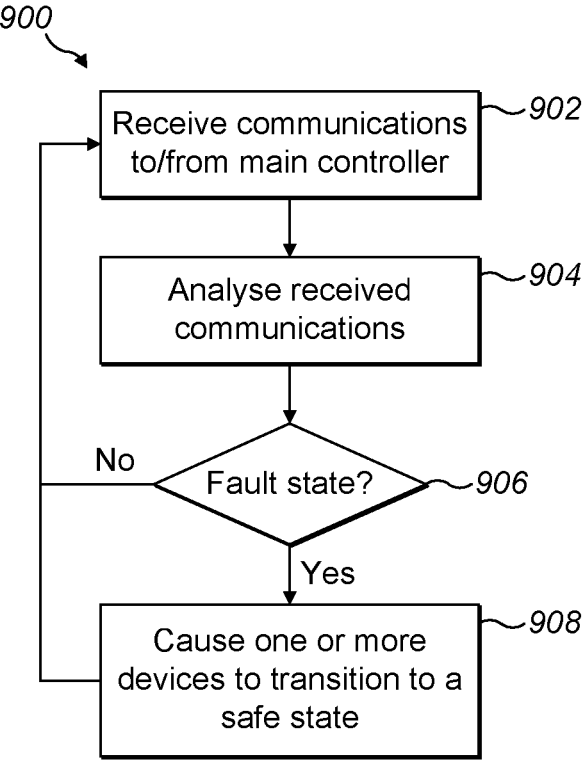
FIG. 9 is a flow diagram of an example method of monitoring the communications to and from the main controller to detect a fault in the system, which may be implemented by the safety monitor of FIG. 8.

Reference is now made to FIG. 9 which illustrates an example method 900 of detecting that a surgical robot system 300, such as the surgical robot system 300 of FIG. 3, is in a fault state, which may be implemented by the safety monitor 316. The method 900 begins at block 902 where the safety monitor 316 receives a copy of at least a portion of the communications to and/or from the main controller 312. As described above, where the control system 306 comprises a safety device 314, the copy of the at least a portion of the communications to and/or from the main controller 312 may be received from the safety device 314. The method 900 then proceeds to block 904 where the safety monitor 316 analyses the received communications to determine whether the devices in the system are operating as expected. The method 900 then proceeds to block 906 where it is determined, based on the analysis performed in block 904, whether the surgical robot system 300 is in a fault state. If it is determined at block 906 that the surgical robot system 300 is in a fault state, the method 900 proceeds to block 908 where the safety monitor 316 causes one or more devices in the surgical robot system to transition to a safe state. If, however, it is determined at block 906 that the surgical robot system is not in a fault state, the method 900 may end or the method 900 may proceed back to block 902.

Example fault states that the safety monitor 316 may be configured to detect include, but are not limited to:

A device running a software version that is not compatible with the software version running on the main controller;

The frequency of communications from a device to the main controller is below a predetermined threshold or the frequency of communication from a main controller of a device is below a predetermined threshold;

The main controller sends position or pose commands to a surgical robot arm that is not in a predetermined state (e.g. an engaged state);

The calculations performed by the main controller are not consistent with the state of the system—to verify a calculation performed by the main controller, the safety monitor may perform the reverse calculation of the main controller;

More than one surgical robot arm reporting the same unique identifier;

A surgical robot arm is reporting a unique identifier that does not match the unique identifier that is associated with that surgical robot arm displayed in a graphical user interface on the display of the operator console; and The surgical robot arm commanding a surgical robot arm to move between a first position and a second position, wherein moving between the first and second position would cause the surgical robot arm to exceed a maximum speed.

It will be evident to a person of skill in the art that these are examples only, and that the safety monitor 316 may be configured to detect additional and/or different fault states from the communications to and/or from the main controller 312. More detailed example fault states which may be detected by the safety monitor 316 are described below.

In some cases, the safety monitor 316 may also be able to confirm that its own characteristics (e.g. software version) are compatible with the characteristics of the main controller 312 and/or the safety device 312.

Main Controller—Surgical Robot Arm—General

In some cases, both the surgical robot arm (e.g. an arm controller thereof) and the main controller may run, or execute, software and the version of the software that the arm or the main controller is currently running may be included in communications from that device. In some cases, certain versions of the arm controller software may only be compatible with certain versions of the main controller software. In these cases, the safety monitor 316 may be configured to: determine, from the communications to and from the main controller, whether the main controller has established a communications connection with a surgical robot arm (e.g. an arm controller thereof); and if it is determined that the main controller has established a communication connection with a surgical robot arm, determine, from the communications to and from the main controller, whether the version of software that the surgical robot arm is running is compatible with the version of software that the main controller is running. If it is determined that the software versions are not compatible the safety monitor 316 may be configured to determine that there is a fault state. In response to determining that there is such a fault state, the safety monitor 316 may cause the surgical robot arm to transition to a safe state. In some cases, the safety monitor 316 may be configured to cause the surgical robot arm to transition to a safe state by causing the safety device 314 to filter all communications between the particular surgical robot arm and the main controller.

In some cases, a surgical robot arm (e.g. the arm controller thereof) is expected to, when operating as expected, respond to a control communication from the main controller within a predetermined time period (e.g. 1000 microseconds). In these cases, the safety monitor 316 may be configured to verify that the latency between a control communication from the main controller 312 to a surgical robot arm (e.g. an arm controller thereof) and the return communication does not exceed the predetermined threshold (e.g. 1000 milliseconds). In some cases, the main controller may be configured to, when it issues a control command to a surgical robot arm, include a latency counter in the communication, and the surgical robot arm (e.g. the arm controller thereof) is configured to include the latency counter in its response to the control communication. In these cases, the safety monitor 316 may be configured to identify the latency between a control packet issued by the main controller 312 to a surgical robot arm (e.g. the arm controller thereof) and the surgical robot's response from the latency counter. If the safety monitor 316 determines that the latency exceeds the predetermined threshold, the safety monitor 316 may determine that the surgical robot system 300 is in a fault state. In response to determining such a fault state, the safety monitor 316 may be configured to cause the surgical robot arm to transition to a safe state. In some cases, the safety monitor 316 may be configured to cause the surgical robot arm to transition to a safe state by causing the safety device 314 to filter all communications between the particular surgical robot arm and the main controller.

In some cases, when the main controller is issuing commands to a surgical robot arm (e.g. an arm controller thereof) which causes the surgical robot arm to move (which may be referred to herein as pose commands), the main controller may be configured to, when operating as expected, issue pose commands to the surgical robot arm at a specific frequency (e.g. 2.5 kHz+/−20%) and the surgical robot arm is configured to, when operating as expected, generate responses to the pose commands at the same frequency (e.g. 2.5 KHz+/−20%). In these cases, the safety monitor 316 may be configured to determine, from the communications to and from the main controller, when the main controller 312 is issuing pose commands to a surgical robot arm. In some cases, communications from the main controller and a surgical robot arm may have a field which indicates whether the communication comprises a pose command, and the safety monitor 316 may be configured to determine from this field whether the main controller is issuing pose commands to a surgical robot arm. If the safety monitor 316 determines that the main controller 312 is issuing pose commands to a surgical robot arm, the safety monitor may determine, from the communications to and from the main controller whether the main controller 312 is issuing pose commands at the predetermined frequency; and whether the relevant surgical robot arm is issuing or sending responses to the pose commands at the predetermined frequency. In some cases, the safety monitor may be configured to determine that the main controller 312 or the relevant surgical robot arm is not issuing pose commands or responses at the predetermined frequency if the frequency of the pose command or responses is below the predetermined frequency for a predetermined number (e.g. 3) of consecutive time windows of a predetermined length (e.g. 5 ms).

If the safety monitor 316 determines that the main controller 312 is not issuing pose commands at the predetermined frequency, or that the relevant surgical robot arm is not sending responses to pose commands at the predetermined frequency, the safety monitor 316 may determine that the surgical robot system 300 is in a fault state. In response to determining that there is such a fault state, the safety monitor 316 may be configured to cause the relevant surgical robot arm to transition to a safe state. In some cases, the safety monitor 316 may be configured to cause the surgical robot arm to transition to a safe state by causing the safety device 314 to filter all communications between the relevant surgical robot arm and the main controller.

In some cases, the communications transmitted from the main controller to the surgical robot arm(s) may include a field which indicates the time at which the communication was transmitted by the main controller. When the main controller is working as expected, the times indicated in that field should be increasing. In these cases, the safety monitor 316 may be configured to monitor this field and determine that the surgical robot system 300 is in a fault state if the times are not increasing. In response to determining such a fault state, the safety monitor 316 may be configured to cause all of the surgical robot arms to transition to a safe state. In some cases, the safety monitor may be configured to cause the surgical robot arms to transition to a safe state by causing the safety device 314 to filter all communications between the main controller and all surgical robot arms.

In some cases, the main controller 312 may be configured to, when operating as expected, only send pose commands to a surgical robot arm that is in a particular mode, which may be referred to herein as a surgical engageable mode. In some cases, a surgical robot arm may be in a surgical engageable mode if it is currently linked to an input device (e.g. hand controller) that is being controlled by an operator. In these cases, the safety monitor may be configured to determine, from the communications to and from the main controller, whether the main controller ceases sending pose commands to any surgical robot arm within a predetermined time (e.g. 2 ms) of the surgical robot no longer being in the particular mode (e.g. surgical engageable mode). If the safety monitor determines that the main controller has sent a pose command to a surgical robot arm more than the predetermined time period after the arm ceased to be in the particular mode (e.g. surgical engageable mode) the safety monitor 316 may determine that the surgical robot system is a fault state. In response to determining that there is such a fault state, the safety monitor may be configured to cause the relevant surgical robot arm to transition to a safe state. In some cases, the safety monitor may be configured to cause the relevant surgical robot arm to transition to a safe state by causing the safety device 314 to filter all communications between the main controller and the relevant surgical robot arm.

As described above, the main controller 312 may be configured to receive information from an input device (e.g. hand controller), when linked to a surgical robot arm, that indicates the position and orientation of the input device. The main controller 312 may then be configured to generate a position and orientation of the wrist of the surgical robot arm (which together may be referred to as the wrist post) based on the position and orientation of the input device, and send wrist position and orientation command information to the surgical robot arm (e.g. the arm controller thereof) to cause the surgical robot arm (e.g. the arm controller thereof) to move the robot such that the wrist of the robot has the desired position and orientation. The surgical robot arm (e.g. the arm controller thereof) may then determine the joint positions and angles to achieve the desired wrist position and orientation and cause the joints to be moved to the determined positions. The surgical robot arm (e.g. arm controller thereof) may then report the final wrist position and orientation, based on the data received from the sensors (e.g. position and/or torque sensors). In some cases, a wrist orientation may be defined by a wrist orientation matrix R. In some cases, when the main controller 312 is working as expected it should not command a surgical robot arm wrist to move its position more than a predetermined amount (e.g. 2 mm) or move its orientation more than a predetermined amount (1.0e-2 element-wise with respect to the matrix R).

In these cases, the safety monitor 316 may be configured to determine, from the communications to and from the main controller, whether the main controller 312 has command a wrist position or a wrist orientation that is more than a predetermined amount (e.g. 2 mm) from the reference wrist position reported by the surgical robot arm (e.g. arm controller thereof) before the main controller 312 issued the command, or more than a predetermined amount (e.g. 1.0e-2 element-wise) from the reference wrist orientation reported by the surgical robot arm. If the safety monitor 316 determines that the main controller has sent a wrist position or wrist orientation command to the surgical robot arm where the difference in position or orientation is greater than a predetermined threshold from the reported reference position or orientation of the wrist, the safety monitor 316 may determine that the surgical robot system 300 is in a fault state. In response to determining that there is such as fault state, the safety monitor may be configured to cause the relevant surgical robot arm (e.g. the arm controller thereof) to transition to a safe state. In some cases, the safety monitor may be configured to cause the relevant surgical robot arm to transition to a safe state by causing the safety device 314 to filter all communications between the main controller and the relevant surgical robot arm.

In some cases, the safety monitor 316 may also be configured to verify, from the communications to and from the main controller, that any wrist orientation matrix R transmitted to a surgical robot arm (e.g. an arm controller thereof) as part of a wrist orientation command is properly formed—i.e. that it is orthogonal. The main controller 312 may generate a non-orthogonal matrix due to, for example, computation errors, signal interference or other types of errors. A wrist orientation matrix R may be deemed to be properly formed (i.e. orthogonal) if R*transpose(R)=identity matrix within a certain threshold (e.g. 1.0e-6 element-wise). If the safety monitor 316 determines that a wrist orientation matrix R transmitted to a surgical robot arm (e.g. an arm controller thereof) as part of a wrist orientation command is not properly formed the safety monitor 316 may determine that the surgical robot system is a fault state. In response to detecting such a fault state, the safety monitor may be configured to cause the relevant surgical robot arm (e.g. the arm controller thereof) to transition to a safe state. In some cases, the safety monitor may be configured to cause the relevant surgical robot arm to transition to a safe state by causing the safety device 314 to filter all communications between the main controller and the relevant surgical robot arm.

Figure 10:
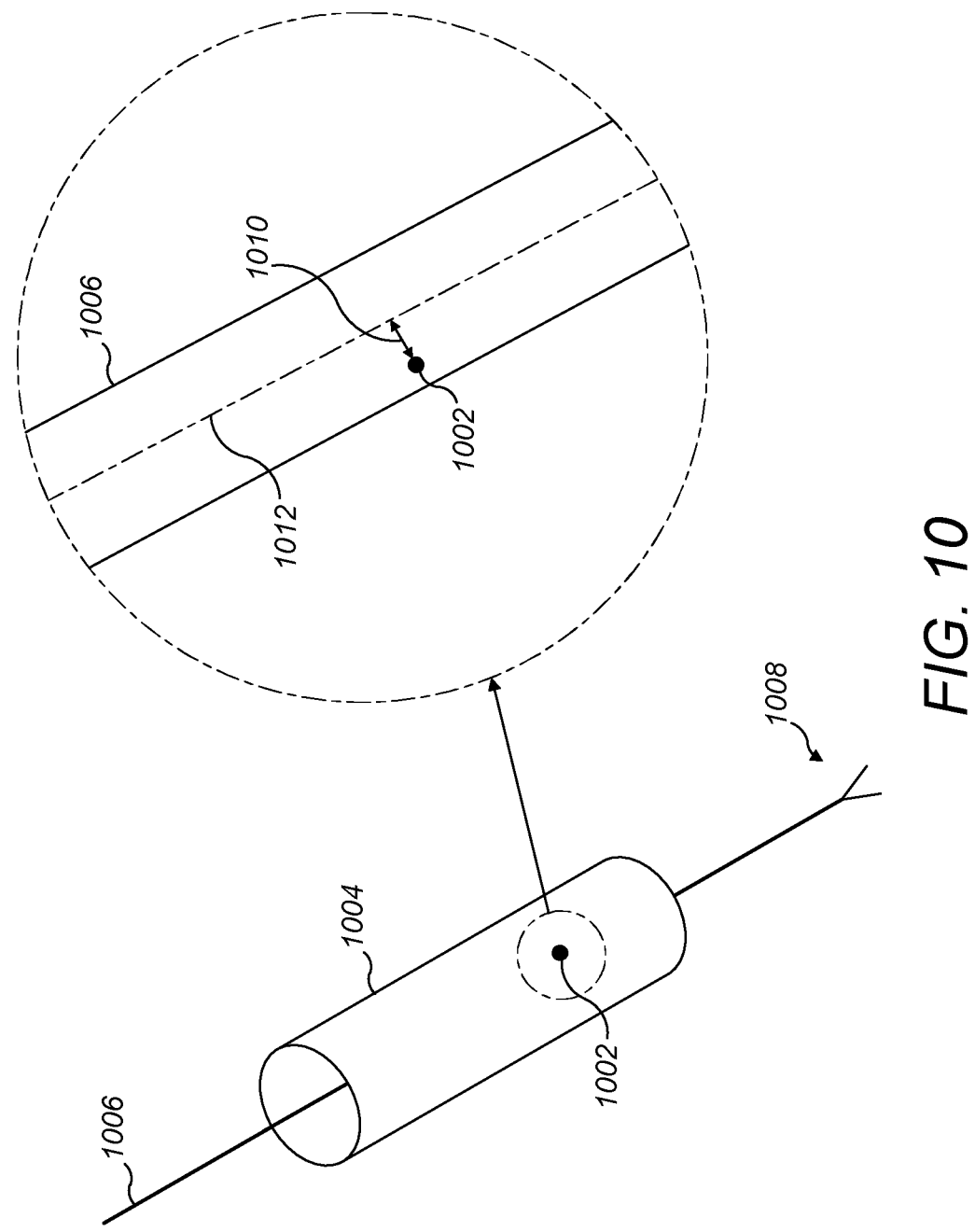
FIG. 10 is a schematic diagram illustrating a virtual pivot point of a port.

As described above with respect to FIG. 1, when the surgical robot system is being used to perform a surgical procedure, a surgical instrument attached to a surgical robot arm may penetrate the body of the patient at a port so as to access the surgical site. In some cases, as shown in FIG. 10, a point 1002 within the port 1004 which the shaft 1006 of a surgical instrument 1008 preferably should pass through, so as to minimize the force or pressure applied to the port and thus the patient, may be determined. Such a point 1002 may be referred to herein as a virtual pivot point (VPP). An example method of identifying the VPP is described in the Applicant's UK Patent No. GB2533004, which is herein incorporated by reference in its entirety. In such cases, the main controller may be configured to control surgical robot arms such that the shaft of any instrument attached thereto passes through the corresponding VPP.

The safety monitor 316 may be provided with information identifying the VPP of each port and the safety monitor 316 may be configured to monitor the communications to and from the main controller to determine if the main controller issues instructions or commands to a surgical robot arm which would cause the surgical robot arm to move to a position in which the perpendicular distance 1010 from the centre line 1012 of the shaft 1006 of the instrument 1008 attached to the surgical robot arm to the VPP 1002 is greater than a predetermined threshold (e.g. 35 mm). If the safety monitor 316 determines that the perpendicular distance exceeds the predetermined threshold, the safety monitor 316 may determine that the surgical robot system 300 is a fault state. In response to detecting such a fault state, the safety monitor 316 may be configured to cause the relevant surgical robot arm to transition to a safe state. In some cases, the safety monitor may be configured to cause the relevant surgical robot arm to transition to a safe state by causing the safety device 314 to filter all communications between the main controller and the relevant surgical robot arm.

To ensure that the surgical instrument attachment portion of a surgical robot arm is not pressing on the surgical port, and thus the patient, the safety monitor 316 may also, or alternatively, be configured to monitor the communications to and from the main controller 312 to determine if the main controller issues instructions or commands to a surgical robot arm that would cause the surgical robot arm to move to a position in which the distance between the base of the shaft (the portion of the shaft closest to the surgical instrument attachment) and the VPP for the corresponding port to be less than a predetermined threshold (e.g. 10 mm). If the safety monitor 316 determines that the distance falls below the predetermined threshold, the safety monitor 316 may determine that the surgical robot system 300 is in a fault state. In response to determining that there is such a fault state, the safety monitor 316 may be configured to cause the relevant surgical robot arm to transition to a safe state. In some cases, the safety monitor may be configured to cause the relevant surgical robot arm to transition to a safe state by causing the safety device 314 to filter all communications between the main controller and the relevant surgical robot arm.

In some cases, each surgical robot arm in a surgical robot system may be allocated a unique identifier that is presented to the operator. For example, in some cases, each surgical robot in a surgical robot system may be allocated a unique colour and the surgical robot arms are configured to display their allocated colour, and each surgical robot arm may be identified by their unique colour in the display of the operator console. For example, each surgical robot may have a light emitting diode (LED) or set of LEDs which can be configured to display one of a plurality of colours. In these cases, the surgical robots may be configured to include their assigned unique identifier (e.g. assigned colour) in communications to the main controller. If multiple surgical robot arms indicate that they have been assigned the same unique identifier (e.g. colour) this may cause problems or confusion when the operator (e.g. surgeon) is trying to select which of the arms to control. Accordingly, the safety monitor 316 may be configured to monitor the communications to and from the main controller to determine if multiple surgical robots indicate the same unique identifier (e.g. colour) within a predetermined window (e.g. 100 milliseconds). If the safety monitor 316 determines that more than one surgical robot arm has reported the same unique identifier (e.g. colour) the safety monitor 316 may determine that the surgical robot system 300 is in a fault state. In response to detecting such a fault state, the safety monitor 316 may be configured to cause the relevant surgical robot arms (i.e. the surgical robot arms reporting the same unique identifier) to transition to a safe state. In some cases, the safety monitor may be configured to cause the relevant surgical robot arms to transition to a safe state by causing the safety device 314 to filter all communications between the main controller and the relevant surgical robot arms.

As described above, in some cases, the main controller may provide the unique identifier of each surgical robot arm to the display (e.g. video processor thereof) of the operator console so that each surgical robot arm can be identified by the unique identifier in the display In these cases, in addition, or alternatively, to detecting that more than on surgical robot arm is reporting the same unique identifier, the safety monitor 316 may be configured to monitor the communications to and from the main controller to determine if the unique identifier reported by each surgical robot arm matches the unique identifier reported to the display of the operator console for that surgical robot arm. If the safety monitor 316 determines that the unique identifier (e.g. colour) reported by a surgical robot arm does not match the unique identifier (e.g. colour) provided to the display for the surgical robot arm, the safety monitor 316 may determine that that the surgical robot system 300 is in a fault state. In response to detecting such a fault state, the safety monitor 316 may be configured to cause the relevant surgical robot arm (i.e. the surgical robot arm with the mismatched unique identifier) to transition to a safe state. In some cases, the safety monitor 316 may be configured to cause the relevant surgical robot arm to transition to a safe state by causing the safety device 314 to filter all communications between the main controller and the relevant surgical robot arm.

Surgical robot systems are often used in endoscopic surgery (e.g. laparoscopic surgery), which also may be referred to as minimally invasive surgery. As is known to those of skill in the art, during an endoscopic procedure the surgeon inserts an endoscope through a small incision or natural opening in the body, such as, but not limited to, the mouth or nostrils. An endoscope is a rigid or flexible tube with a tiny camera attached thereto that transmits real-time images to a video monitor (e.g. display 206) that the surgeon uses to help guide his tools through the same incision/opening or through a different incision/opening. The endoscope allows the surgeon to view the relevant area of the body in detail without having to cut open and expose the relevant area. This technique allows the surgeon to see inside the patient's body and operate through a much smaller incision than would otherwise be required for traditional open surgery. Accordingly, in a typical robotic endoscopic surgery there is an endoscope attached to one surgical robot arm and one or more surgical instruments, such as a pair of pincers and/or a scalpel, attached to one or more other surgical robot arms. Since the endoscope provides the operator (e.g. surgeon) with a view of the surgical site it may not be safe to operate a surgical robot unless an endoscope is attached to one of the surgical robot arms and is operating as expected.

Where the surgical robot arms are configured to report the type of tool (e.g. surgical instrument or endoscope) attached thereto, the safety monitor 316 may be configured to determine, from the communications to and from the main controller, whether there is an endoscope attached to one of the surgical robot arms and if so, whether the endoscope is operating as expected. If the safety monitor 316 determines that there is not an endoscope attached to one of the surgical robot arms, or that the attached endoscope is not working as expected, the safety monitor 316 may determine that the surgical robot system 300 is in a fault state. In response to detecting such as fault state, the safety monitor 316 may be configured to cause all of the surgical robot arms to transition to a safe state. In some cases, the safety monitor may be configured to cause the surgical robot arms to transition to a safe state by causing the safety device 314 to filter all communications between the main controller and the surgical robot arms.

As described above, in some cases, an operator (e.g. surgeon) may be able to control the movement and/or position of a surgical robot arm (and a surgical instrument/endoscope attached thereto) by providing input via an input device, such as, but not limited to a hand controller. In some cases, the surgeon can use an input device (e.g. hand controller) to control a specific surgical robot arm by linking the input device (e.g. hand controller) to the specific surgical robot arm (e.g. via the operator console). In some cases, if the surgical robot system detects that an endoscope is not attached to a surgical robot arm, or the attached endoscope is not working as expected then any hand controllers should be disconnected from the surgical robot arms within a predetermined time period (e.g. 5 ms). In these cases, the safety monitor 316 may be configured to determine, from the communications to and from the main controller, whether there is an endoscope attached to one of the surgical robot arms and if so, whether the endoscope is operating as expected. If the safety monitor 316 determines that there is not an endoscope attached to one of the surgical robot arms, or that the attached endoscope is not working as expected, the safety monitor 316 may determine, from the communications to and from the main controller, that the surgical robot system 300 is in a fault state, if after a predetermined time after the detection (e.g. 5 ms) that there is still an input device linked to a surgical robot system. In response to detecting such a fault state, the safety monitor 316 may be configured to cause all of the surgical robot arms to transition to a safe state. In some cases, the safety monitor may be configured to cause the surgical robot arms to transition to a safe state by causing the safety device 314 to filter all communications between the main controller and the surgical robot arms.

In some cases, it may not be desirable to move the surgical robot arms too quickly or too fast. Accordingly, the main controller 312 may be configured to, when working as expected, cause a surgical robot arm (e.g. the wrist of the surgical robot arm) to move no faster than a predetermined speed limit (e.g. 0.25 m/s). In such cases, the safety monitor 316 may be configured to determine, from the communications to and from the main controller, whether the main controller is causing a surgical robot arm to move faster than the predetermined speed limit (within an acceptable tolerance such as, but not limited to, +/−10%). In some cases, the main controller 312 may be configured to cause a surgical robot to arm to move by issuing a sequence of position or pose command, each position or pose command indicating the position or pose that the surgical robot arm (or the wrist of the surgical robot arm is to move to). In these cases, the safety monitor 316 may be configured to determine that the main controller has issued a command which would cause a surgical robot arm to move faster than the predetermined speed limit if the safety monitor detects that the difference between two consecutive poses commanded by the main controller 312 would result in a speed that exceeds the predetermined speed limit (within a threshold e.g. 10%).

If the safety monitor 316 determines that the main controller has issued a command which would cause a surgical robot arm (e.g. a wrist thereof) to exceed the predetermined speed limit the safety monitor 316 may determine that the surgical robot system 300 is in a fault state. In response to detecting such a fault state, the safety monitor 316 may be configured to cause the relevant surgical robot arm (the surgical robot would be caused to exceed the predetermined speed threshold) to transition to a safe state. In some cases, the safety monitor may be configured to cause a surgical robot arm to transition to a safe state by causing the safety device 316 to filter all communications between the main controller and the relevant surgical robot arm.

Main Controller—Surgical Robot Arm with Surgical Instrument Attached Thereto

In some cases, there may be different rules which are applied to surgical robot arms with a surgical instrument attached thereto, versus a surgical robot arm with an endoscope attached thereto.

As described above, in some cases each surgical robot arm may be assigned a unique identifier (e.g. a unique colour) by the main controller 312. In some cases, the surgical robot arm that has an endoscope attached thereto may consistently be assigned the same unique identifier. In other words, in some cases a specific unique identifier may be reserved for the surgical robot arm that has an endoscope attached thereto. For example, the surgical robot arm that has an endoscope attached thereto may be allocated the white colour. As described above, the surgical robot arms may be configured to include the unique identifier allocated thereto in at least some of the communications to the main controller 312. If a surgical robot arm that does not have an endoscope attached thereto (e.g. it has a surgical instrument attached thereto) is reporting the special unique identifier (e.g. colour) reserved for the endoscope arm, then the system may not be working as expected.

Accordingly, the safety monitor 316 may be configured to determine, from the communications to and from the main controller 312, whether a surgical robot arm that does not have an endoscope attached thereto is reporting the unique identifier (e.g. colour) reserved for the surgical robot arm with an endoscope attached thereto. If the safety monitor 316 determines that a surgical robot arm that is not attached to an endoscope is reporting the unique identifier (e.g. colour) reserved for the surgical robot arm with an endoscope attached thereto, the safety monitor 316 may determine that the surgical robot system 300 is in a fault state. In response to detecting such a fault state, the safety monitor 316 may be configured to cause the relevant surgical robot arm (the surgical robot incorrectly reporting the unique identifier reserved for a surgical robot arm with an endoscope attached thereto) to transition to a safe state. In some cases, the safety monitor 316 may be configured to cause the relevant surgical robot arm to transition to a safe state by causing the safety device 314 to filter all communications between the main controller and the relevant surgical robot arm.

In some cases, the main controller 312 may be configured to, when it is working as expected, control a maximum number (e.g. three or four) of instrument surgical robot arms (i.e. a surgical robot arm with a surgical instrument (vs an endoscope) attached thereto). In these cases, the safety monitor 316 may be configured to determine, from the communications to and from the main controller 312, whether the main controller 312 has issued control commands to more than the maximum number of instrument surgical robot arms within a predetermined period (e.g. a 1 millisecond window). If the safety monitor 316 determines that the main controller 312 has issued commands to more than the maximum number of instrument surgical robot arms the safety monitor 316 may determine that the surgical robot system 300 is in a fault state. In response to detecting such a fault state, the safety monitor 316 may be configured to cause all the surgical robot arms to transition to a safe state. In some cases, the safety monitor 316 may be configured to cause the surgical robot arms to transition to a safe state by causing the safety device 314 to filter all communications between the main controller and the surgical robot arms.

In some cases, one or more of the surgical instruments attached to a surgical robot arm may be actuable—i.e. the end effector of the surgical instrument may be actuable or moveable. In some cases, drive may be transferred from the surgical robot to the instrument to cause movement of the end effector through one or more drive interface elements on the instrument attachment, which engage corresponding instrument interface elements on the instrument. In some cases, the drive interface elements may be linearly moveable. The main controller 316 may be configured to command the surgical robot arm to move the end effector of an attached instrument to a desired pose or position based on the inputs received from the input devices by commanding the surgical robot arm to move one or more of the drive interface elements to certain positions. To ensure that the main controller 316 does not issue a command that would cause an instrument end effector to move at a velocity that exceeds a predetermined threshold, the safety monitor 316 may be configured to determine, from the communication to and/or from the main controller 316, whether the commanded position of any of the drive interface elements differs from the reference position of that drive interface element reported by the surgical robot arm (e.g. arm controller thereof) prior to the command more than a predetermined amount (e.g. 0.1 mm). If the safety monitor 316 determines that the main controller 312 has issued command that would cause one or more of the drive interface elements to move more than a predetermined amount, the safety monitor 316 may determine that the surgical robot system 300 is in a fault state. In response to detecting such a fault state, the safety monitor 316 may be configured to cause the relevant surgical robot arm to transition to a safe state. In some cases, the safety monitor 316 may be configured to cause the surgical robot arms to transition to a safe state by causing the safety device 314 to filter communications between the main controller and the relevant surgical robot arm.

As described above, in some cases, an operator (e.g. surgeon) may be able to control the movement and/or position of a surgical robot arm (and a surgical instrument/endoscope attached thereto) by providing input via an input device, such as, but not limited to a hand controller. In some cases, the surgeon can use an input device (e.g. hand controller) to control a specific surgical robot arm by linking the input device (e.g. hand controller) to the specific surgical robot arm (e.g. via the operator console). If the system is working as expected an input device (e.g. hand controller) is linked to a surgical robot arm; the operator (e.g. surgeon) then provides inputs to the main controller, via the input device, indicating the desired position/movement of the surgical robot arm; and then the main controller issues commands to the surgical robot arm to move as desired. Accordingly, a main controller should, when it is operating as expected, only issue control commands to a surgical robot arm that is actively linked to an input device (e.g. hand controller).

In some cases, the main controller 312 may be configured to include in any communications issued to a surgical robot arm to cause movement thereof, the input device (e.g. hand controller) currently linked to the surgical robot arm. The safety monitor 316 may then be configured to determine, from the communications to and from the main controller 312, whether the main controller 312 has issued a control command to a surgical robot arm without specifying the input device (e.g. hand controller) currently linked to that surgical robot arm. If the safety monitor 316 determines that the main controller 312 has issued command to a surgical robot arm without specifying the input device (e.g. hand controller) currently linked to that surgical robot arm the safety monitor 316 may determine that the surgical robot system 300 is in a fault state. In response to detecting such a fault state, the safety monitor 316 may be configured to cause the relevant surgical robot arm to transition to a safe state (e.g. the surgical robot arm that the main controller issued a pose command to without specifying the input device (e.g. hand controller) linked thereto). In some cases, the safety monitor 316 may be configured to cause the relevant surgical robot arm to transition to a safe state by causing the safety device 314 to filter all communications between the main controller and the relevant surgical robot arms.

As described above, in some cases the operator may be able to select which surgical robot arm is to be controlled using a particular input device (e.g. hand controller) via, for example, a graphical user interface presented to the operator on the display of the operator console. In some cases, the safety monitor 316 may be configured to identify, from the communications to and from the main controller 312, the surgical robot arm that the operator has linked to an input device (e.g. hand controller), and determine whether the main controller believes that the surgical robot arm is linked to a different input device (e.g. hand controller). If the safety monitor 316 determines that the main controller 312 has indicated that a surgical robot arm is connected to a different input device (e.g. hand controller) than that linked to the surgical robot arm by the operator, the safety monitor 316 may determine that the surgical robot system 300 is in a fault state. In response to detecting such a fault state, the safety monitor 316 may be configured to cause all the surgical robot arms to transition to a safe state. In some cases, the safety monitor 316 may be configured to cause the surgical robot arms to transition to a safe state by causing the safety device 314 to filter all communications between the main controller and the surgical robot arms.

In some cases, even after a surgical robot arm has been linked to an input device (e.g. hand controller) by the operator (e.g. via a graphical user interface) the input device may only be used to control the linked surgical robot arm if the input device (e.g. hand controller) is in a particular state, which may be referred to herein as an engaged state. In some cases, an input device (e.g. hand controller) may only be in the particular state (e.g. engaged state) if one or more conditions are satisfied, such as, but not limited to, the operator is in contact with the input device (e.g. the operator's palm is engaged with a hand controller), there are no faults with the hand controller, and the operator has not indicated (e.g. via special button press) that they wish to put the input device in a disengaged state. Accordingly, if the main controller 312 issues move instructions (e.g. a pose command) to a surgical robot whose linked input device (e.g. hand controller) is not in the predetermined state (e.g. engaged state) for controlling the surgical robot arm then that may signify that the main controller is not operating as expected.

Accordingly, the safety monitor 316 may be configured to identify, from the communications to and from the main controller 312, the current state of the input devices and determine whether the main controller has issued move instructions (e.g. a pose command) to a surgical robot arm whose linked input device is not in the predetermined state (e.g. engaged state) for controlling a surgical robot arm. If the safety monitor 316 determines that the main controller 312 has issued move instructions to a surgical robot arm whose linked input device is not in the predetermined state, the safety monitor 316 may determine that the surgical robot system 300 is in a fault state. In response to detecting such a fault state, the safety monitor 316 may be configured to cause the relevant surgical robot arm (the surgical robot arm that the main controller incorrectly issued move instructions to) to transition to a safe state. In some cases, the safety monitor 316 may be configured to cause the relevant surgical robot arm to transition to a safe state by causing the safety device 314 to filter all communications between the main controller and the relevant surgical robot arm.

In some cases, the main controller 312 may be configured to translate the movement of an input device (e.g. hand controller) to movement of an instrument end effector by applying a scale factor to the input device movement. For example, if the movement of an input device were represented by X then the main controller 312 may cause the end effector to move kX where k is the scaling factor. In some cases, the scale factor may be included in communications from the main controller and a surgical robot arm (e.g. controller thereof) for the benefit of the safety monitor 316. In such cases, the safety monitor 316 may be configured to determine, from the communications to and/or from the main controller 312, whether the main controller 312 has issued pose commands to a surgical robot arm that are not consistent with one of a plurality of acceptable, or possible, scaling factors. If the safety monitor 316 determines that the main controller 312 has issued command instructions to a surgical robot arm that are not consistent with one of the plurality of acceptable or possible scaling factors, the safety monitor 316 may determine that the surgical robot system 300 is in a fault state. In response to detecting such a fault state, the safety monitor 316 may be configured to cause the relevant surgical robot arm (the surgical robot arm that the main controller incorrectly issued move instructions to) to transition to a safe state. In some cases, the safety monitor 316 may be configured to cause the relevant surgical robot arm to transition to a safe state by causing the safety device 314 to filter all communications between the main controller and the relevant surgical robot arm.

In some cases, the operator (e.g. surgeon) may be configured to indicate the desired location and/or movement of a surgical instrument attached to a surgical robot arm by moving an input device (e.g. hand controller). The main controller 312 may then be configured to determine a pose (i.e. position (x,y,z) and orientation) of the surgical instrument tip based on the inputs received from the input device (e.g. hand controller), the endoscope pose (i.e. position (x,y,z) and orientation), and a scale factor associated with the operator input (described above); and then determine a wrist pose and instrument yaw and instrument pitch to achieve the calculated instrument tip pose based on the VPP and command the surgical robot arm to move to the determined wrist pose. As described above, the VPP is a point through which the shaft of the instrument should preferably pass through to reduce the force applied to the port, and thus the patient.

In some cases, the main controller 312 may be configured to output its calculated instrument tip pose. In such cases, the safety monitor 316 may be configured to verify the calculation of the surgical instrument tip pose by the main controller 312 based on the communications to and from the main controller. Specifically, the safety monitor 316 may be configured to identify, from the communications to and from the main controller 312, the inputs provided by the input device (e.g. hand controller inputs), the endoscope pose (i.e. position and orientation), the scale factor (described above), and the surgical instrument tip pose calculated by the main controller 312. The safety monitor 316 may then perform the reverse calculation from the calculated instrument tip pose to identify an estimate of the input. The safety monitor 316 may then be configured to compare the actual inputs to the estimated inputs to determine whether they are within a predetermined acceptable range of each other. If the safety monitor determines that the actual inputs and the estimated inputs are not within the predetermined acceptable range of each other the safety monitor 316 may determine that the surgical robot system 300 is in a fault state. In response to detecting such a fault state, the safety monitor 316 may be configured to cause the relevant surgical robot arm (the surgical robot arm that the main controller incorrectly issued move instructions to) to transition to a safe state. In some cases, the safety monitor 316 may be configured to cause the relevant surgical robot arm to transition to a safe state by causing the safety device 314 to filter all communications between the main controller and the relevant surgical robot arm.

In some cases, the safety monitor 316 may also be configured to verify the calculation of the instrument yaw, the instrument pitch and the wrist pose (i.e. position and orientation) by the main controller based on the communications to and from the main controller 312. Specifically, the safety monitor 316 may be configured to identify, from the communications to and from the main controller, the surgical instrument tip pose (i.e. position and orientation) calculated by the main controller 312, the pitch and yaw of the instrument calculated by the main controller 312, and the wrist position calculated by the main controller 312. The safety monitor 316 then be configured to perform the reverse calculation from the calculated instrument pitch, instrument yaw, wrist pose and VPP to identify an estimate of the surgical instrument tip pose. The safety monitor 316 may then be configured to compare the estimated instrument tip pose to the instrument tip pose calculated by the main controller and determine whether they are within a predetermined acceptable range of each other. If the safety monitor 316 determines that the instrument tip pose calculated by the main controller and the estimated instrument top pose are not within the predetermined acceptable range of each other, the safety monitor 316 may determine that the surgical robot system 300 is in a fault state. In response to detecting such a fault state, the safety monitor 316 may be configured to cause the relevant surgical robot arm (the surgical robot arm that the main controller issued a move instruction to) to transition to a safe state. In some cases, the safety monitor 316 may be configured to cause the relevant surgical robot arm to transition to a safe state by causing the safety device 314 to filter all communications between the main controller and the relevant surgical robot arm.

As described above, some instruments may be actuable by transferring drive from the surgical robot arm to the instrument attached thereto by one or more drive interface elements which interact with corresponding instrument interface elements of the surgical instrument. In some cases, once the main controller 312 has calculated the instrument pitch, the instrument yaw and instrument spread (e.g. the spread of the jaws), the main controller 312 may be configured to calculate the drive element positions so as to achieve the desired instrument pitch, yaw and spread. In such cases, the safety monitor 316 may be configured to verify the calculation of the drive element positions by the main controller based on the communications to and from the main controller.

Specifically, the safety monitor 316 may be configured to identify, from the communications to and from the main controller, the instrument pitch, instrument yaw, instrument spread, and drive element positions calculated by the main controller 312. The safety monitor 312 may then be configured to calculate an estimate of the drive element positions from the instrument pitch, yaw and spread and determine if the estimated drive element positions are within a predetermined distance (1.0e-6 m) of the calculated drive element positions. If the safety monitor determines that the estimated drive element positions are not sufficiently close to the calculated drive element positions the safety monitor 316 may determine that the surgical robot system 300 is in a fault state. In response to detecting such a fault state, the safety monitor 316 may be configured to cause the relevant surgical robot arm to transition to a safe state. In some cases, the safety monitor 316 may be configured to cause the relevant surgical robot arm to transition to a safe state by causing the safety device 314 to filter all communications between the main controller and the relevant surgical robot arm.

In some cases, one or more of the surgical instruments attached to a surgical robot arm may be actuable. Some actuable instruments, such as a grasper (which may be alternatively referred to as a pincer) comprise a plurality of elements (e.g. jaws), which may be moveable between an open position and a closed position. The movement of the elements may be controlled by a special input on the input devices. For example, each input device may have a lever, or another moveable component or a set of components (e.g. a slider which can be moved in a least two directions, or opposing members which can be squished together or brought in close proximity), which when moved in one direction or manner (e.g. pressed inward) causes the elements to move towards a closed position, and when moved in a different direction or manner (e.g. pressed or pulled outward) causes the elements to move towards an open position. The main controller may be configured to map position of the lever to a position of the elements of the instrument via one or more control parameters and cause the elements to be moved to the calculated position. In such cases, the safety monitor 316 may be configured to verify the calculation of the position of the elements by the main controller based on the communications to and from the main controller.

Specifically, the safety monitor 316 may be configured to identify, from the communications to and from the main controller (i) the desired position of the elements (e.g. jaws) as calculated by the main controller, and (ii) the position of the relevant input (e.g. lever); and independently calculate from the relevant input (e.g. lever) the position of the elements (e.g. jaws). The safety monitor 316 may then be configured to determine if the desired position of the elements (e.g. jaws) as calculated by the main controller is within a predetermined distance (e.g. 0.015 radians) of the position of the elements (e.g. jaws) as calculated by the safety monitor 315. In some cases, the position of the elements may be defined by the angle between the elements. If the safety monitor 316 determines that the desired position of the element (e.g. jaws) as calculated by the main controller is not within a predetermine distance (e.g. 0.015 radian) of the position of the elements (e.g. jaws) as determined by the safety monitor 316 the safety monitor 316 may determine that the surgical robot system is in a fault state. In response to detecting such a fault state, the safety monitor 316 may be configured to cause the relevant surgical robot arm (e.g. the surgical robot arm to which the relevant actuable instrument is attached) to transition to a safe state. In some cases, the safety monitor 316 may be configured to cause the relevant surgical robot arm to transition to a safe state by causing the safety device 314 to filter all communications between the main controller and the relevant surgical robot arm.

Main Controller—Surgical Robot Arm with Endoscope Attached Thereto

As described above, in some cases, there may be different rules which are applied to surgical robot arms with an endoscope attached thereto, versus a surgical robot arm with a surgical instrument attached thereto.

As described above, in some cases each surgical robot arm may be assigned a unique identifier (e.g. a unique colour) by the main controller 312. In some cases, the surgical robot arm that has an endoscope attached thereto may consistently be assigned the same unique identifier. In other words, in some cases a specific unique identifier may be reserved for the surgical robot arm that has an endoscope attached thereto. For example, the surgical robot arm that has an endoscope attached thereto may be allocated the white colour. As described above, the surgical robot arms may be configured to include the unique identifier allocated thereto in at least some of the communications to the main controller 312. If a surgical robot arm that does not have an endoscope attached thereto (e.g. it has a surgical instrument attached thereto) is reporting the special unique identifier (e.g. colour) reserved for the endoscope arm, then the system may not be working as expected.

Accordingly, the safety monitor 316 may be configured to determine, from the communications to and from the main controller 312, whether a surgical robot arm that has an endoscope attached thereto is not reporting the unique identifier (e.g. colour) reserved for the surgical robot arm with an endoscope attached thereto. If the safety monitor 316 determines that a surgical robot arm that is attached to an endoscope is not reporting the unique identified (e.g. colour) reserved for the surgical robot arm with an endoscope attached thereto, the safety monitor 316 may determine that the surgical robot system 300 is in a fault state. In response to detecting such a fault state, the safety monitor 316 may be configured to cause the relevant surgical robot arm (the surgical robot arm attached to the endoscope) to transition to a safe state. In some cases, the safety monitor 316 may be configured to cause the relevant surgical robot arm to transition to a safe state by causing the safety device 314 to filter all communications between the main controller and the relevant surgical robot arm.

As described above, surgical instruments and/or endoscopes may be releasably attached to a surgical robot arm, such that can be detached from a surgical robot arm even when a surgical robot arm is currently in use in a surgical procedure. A surgical robot arm may itself be able to determine when a surgical instrument or endoscope has been attached thereto and when a surgical instrument or endoscope has been detached therefrom and report a detected attachment or detachment to the main controller. To ensure that the main controller 312 does not issue endoscope position or pose commands to a surgical robot arm to which an endoscope has been detached, the safety monitor 316 may be configured to determine, from the communications to and from the main controller when an endoscope has been detached from a surgical robot arm. If the safety monitor 316 detects that an endoscope has been detached from a surgical robot arm, the safety monitor 316 may determine whether after a predetermined period (e.g. 2 milliseconds) after the detachment the main controller has issued endoscope position command to that surgical robot arm. If the safety monitor 316 determines that the main controller has issued an endoscope position command to that surgical robot arm after the predetermined period, the safety monitor 316 may determine that the surgical robot system 300 is in a fault state. In response to determining that there is such a fault state, the safety monitor 316 may be configured to cause the relevant surgical robot arm (the surgical robot arm from which the endoscope was detached) to transition to a safe state. In some cases, the safety monitor 316 may be configured to cause the relevant surgical robot arm to transition to a safe state by causing the safety device 314 to filter all communications between the main controller and the relevant surgical robot arm.

As described above, in some cases, an operator (e.g. surgeon) may be able to control the movement and/or position of a surgical robot arm (and a surgical instrument/ endoscope attached thereto) by providing input via an input device, such as, but not limited to a hand controller. In some cases, even after a surgical robot arm has been linked to an input device (e.g. hand controller) by the operator (e.g. via a graphical user interface) the input device may only be used to control an endoscope attached to a linked surgical robot arm if the input device (e.g. hand controller) is in a particular state, which may be referred to herein as an engaged state. When an input device (e.g. hand controller) is not in the particular state (e.g. hand controller) the hand controller may be used for another purpose, such as, but not limited to, providing input to a graphical user interface. In some cases, an input device (e.g. hand controller) may only be in the particular state (e.g. engaged state) if one or more conditions are satisfied, such as, but not limited to, the operator is in contact with the input device (e.g. the operator's palm is engaged with a hand controller), there are no faults with the hand controller, and the operator has not indicated (e.g. via special button press) that they wish to put the input device in a disengaged state.

In contrast to a surgical instrument, however, which may be completely controlled by a single input device (e.g. hand controller), an endoscope may be partially controlled by one input device (e.g. hand controller) and partially controlled by another input device (e.g. hand controller). For example, a first input device (e.g. the left hand controller) may be used to control a first set of features of the endoscope (e.g. the pitch and yaw of the endoscope), and a second input device (e.g. the right hand controller) may be used to control a second set of features of the endoscope (e.g. the roll and depth of the endoscope). In such cases, the main controller may not be working as expected if the first input device (e.g. left hand controller) is not in the particular state (e.g. the engaged state) and the main controller issues commands to the relevant surgical robot arm (the surgical robot arm attached to the endoscope) related to the first set of features and/or if the second input device (e.g. right hand controller) is not in the particular state (e.g. the engaged state) and the main controller issues command to the relevant surgical robot arm related to the second set of features.

Accordingly, the safety monitor 316 may be configured to determine, from the communications to and from the main controller 312, whether the first or second input device (e.g. left or right hand controller) is not in the particular state. If the safety monitor 316 determines that the first input device (e.g. left hand controller) is not in the particular state, the safety monitor 316 may determine if the main controller issues commands to the relevant surgical robot arm (i.e. the surgical robot arm attached to the endoscope) related to the first set of features. If the safety monitor 316 determines that the second input device (e.g. right hand controller) is not in the particular state, the safety monitor 316 may determine if the main controller issues command to the relevant surgical robot arm related to the second set of features. If the safety monitor 316 detects either condition, the safety monitor 316 may determine that the surgical robot system 300 is in a fault state. In response to detecting such a fault state, the safety monitor 316 may be configured to cause the relevant surgical robot arm (i.e. the surgical robot arm attached to the endoscope) to transition to a safe state. In some cases, the safety monitor 316 may be configured to cause the relevant surgical robot arm to transition to a safe state by causing the safety device 314 to filter all communications between the main controller and the relevant surgical robot arm.

In some cases, the safety monitor 316 may also be configured to verify that when the main controller instructs a change in pose of a surgical robot arm attached to an endoscope that the instructed change in pose is consistent with the endoscope motion pitch, yaw, roll and change in depth requested by the operator (e.g. via an input device, such as a hand controller). In one example, an instructed pose may be deemed to be consistent with the requested endoscope motion if the requested pitch, yaw and roll are within a predetermined distance (e.g. 0.00001 radians) of the instructed pitch, yaw and roll respectively, and the requested depth is within 2.0e-7 metres of the instructed depth. Specifically, the safety monitor 316 may be configured to determine, from the communications to and from the main controller 312, when an operator (e.g. surgeon) has requested a pose change to the endoscope (e.g. via an input device, such as a hand controller). If the operator (e.g. surgeon) has requested a pose change to the endoscope, the safety monitor 316 may be configured to determine, from the communications to and from the main controller 312, the instructed pose sent to the relevant surgical robot arm (i.e. the surgical robot arm to which the endoscope is attached). The safety monitor 316 whether the instructed post is consistent with the request endoscope motion. If it is determined the instructed pose is not consistent with the requested endoscope motion, then the safety monitor 316 may determine that the surgical robot system is in a fault state. In response to detecting such a fault state, the safety monitor 316 may be configured to cause the relevant surgical robot arm (i.e. the surgical robot arm attached to the endoscope) to transition to a safe state. In some cases, the safety monitor 316 may be configured to cause the relevant surgical robot arm to transition to a safe state by causing the safety device 314 to filter all communications between the main controller and the relevant surgical robot arm.

In some cases, the optical angle of the endoscope may be adjustable. In some cases, the optical angel may be adjustable to one of a plurality (e.g. 3) of predetermined optical angles. In some cases, the translation of operator movements (e.g. movement of the input device (e.g. hand controller)) to instructions that the control the movement of a surgical robot arm (and a surgical instrument attached thereto) may be based on the endoscope optical angle. In these cases, the safety monitor 316 may be configured to determine, from the communications to and from the main controller, whether the optical angle of the endoscope has changed value. Then if the safety monitor 316 determines the optical angle of the endoscope has changed value, the safety monitor 316 may determine, from the communications to and from the main controller that the main controller is not issuing pose instructions to a surgical robot arm, and optionally, whether the new optical angle of the endoscope is one of the plurality of predetermined optical angles. If either of these conditions are satisfied, then the safety monitor 316 may determine that the surgical robot system is in a fault state. In response to detecting such a fault state, the safety monitor 316 may be configured to cause the entire system to transition to a safe state. In some cases, the safety monitor 316 may be configured to cause the entire system to transition to a safe state by causing the safety device 316 to filter all communications to and from the main controller.

Main Controller—Input Device Control Unit

In some cases, the input device (e.g. hand controllers) may have a controller therein that is configured to receive sensor data from one or more sensors in the input device (e.g. hand controller) and determine therefrom a position and orientation of the hand controller within the hand controller frame of reference, and transmit the determined pose and orientation to the main controller. The main controller then converts the position and orientation into commands to control a surgical arm and a surgical instrument/endoscope attached thereto. In some cases, the input device controller may not include a built-in safety monitor. In such cases, the safety monitor may be configured to verify, from the communications to and from the main controller to vary the operation of the input device controllers.

In some cases, both the input devices (e.g. the controller thereof) and the main controller may run, or execute, software and the version of the software that the input device or the main controller is currently running may be included in communication from that device. In some cases, certain versions of the input device controller software may only be compatible with certain versions of the main controller software. In these cases, the safety monitor 316 may be configured to: determine, from the communications to and from the main controller, whether the main controller has established a communications connection with an input device (e.g. a controller thereof); and if it is determined that the main controller has established a communication connection with an input device, determine, from the communications to and from the main controller, whether the version of software that the input device is running is compatible with the version of software that the main controller is running. If it is determined that the software versions are not compatible the safety monitor 316 may be configured to determine that the surgical robot system 300 is in a fault state. In response to determining that there is such a fault state, the safety monitor 316 may cause the relevant input device (e.g. hand controller) to transition to a safe state. In some cases, the safety monitor 316 may be configured to cause the relevant input device to transition to a safe state by causing the safety device 314 to filter all communications between the relevant input device (e.g. hand controller) and the main controller.

In some cases, the main controller may be configured to send a heartbeat signal to each input device (e.g. each input device controller) at a predetermined frequency (e.g. 2.5 kHz). In these cases, an input device (e.g. an input device controller) may be configured to transition into a safe state if it does not receive the heartbeat signal at the predetermined frequency. In these cases, the safety monitor 316 may be configured to determine, from the communication to and from the main controller, whether the main controller is sending each input device a heartbeat signal within predetermined constraints—e.g. within a predetermined threshold (e.g. +/−20%) of the predetermined frequency (e.g. 2.5 kHz) over a predetermined window of time (e.g. 5 milliseconds). If it is determined that the main controller is not sending a heartbeat signal to an input device within the predetermined constraints, the safety monitor 316 may be configured to determine that the surgical robot system 300 is in a fault state. In response to determining that there is such a fault state, the safety monitor 316 may cause the relevant input device (e.g. hand controller) to transition to a safe state. In some cases, the safety monitor 316 may be configured to cause the relevant input device to transition to a safe state by causing the safety device 314 to filter all communications between the relevant input device (e.g. hand controller) and the main controller.

In some cases, an input device (e.g. the controller thereof) is expected to, when operating as expected, respond to a control communication from the main controller within a predetermined time period (e.g. 1000 microseconds). In these cases, the safety monitor 316 may be configured to verify that the latency between a control communication from the main controller 312 to an input device (e.g. a controller thereof) and the return communication does not exceed the predetermined threshold (e.g. 1000 milliseconds). In some cases, the main controller may be configured to, when it issues a control command to a surgical robot arm, include a latency counter (e.g. timestamp) in the communication, and the surgical robot arm (e.g. the arm controller thereof) is configured to include the latency counter in its response to the control communication. In these cases, the safety monitor 316 may be configured to identify the latency between a control packet issued by the main controller 312 to an input device (e.g. the controller thereof) and the input device's response from the latency counter. If the safety monitor 316 determines that the latency exceeds the predetermined threshold the safety monitor 316 may determine that the surgical robot system is in a fault state. In response to detecting such a fault state, the safety monitor 316 may be configured to cause the relevant input device to transition to a safe state. In some cases, the safety monitor 316 may be configured to cause the relevant input device to transition to a safe state by causing the safety device 314 to filter all communications between the relevant input device and the main controller.

As described above, an input device (e.g. hand controller) may be considered engaged if it is linked to a surgical robot arm that is in surgical mode (e.g. a mode in which the surgical robot arm can be controlled by the input device). There may be engaged ok signal for each input device that is generated by the main controller 312 indicates whether the input device is engaged with a surgical robot arm. In such cases, the safety monitor 316 may be configured to verify, from the communications to and from, the main controller that if an 'engaged ok' signal transitions to false that within a predetermined period of time (e.g. 1 ms) the relevant input device (e.g. the controller thereof) indicates that it is in a disengaged stated. If the safety monitor determines that the relevant input device (e.g. controller thereof) does not transition to the disengaged state within the predetermined period of time, the safety monitor 316 may determine that the surgical robot system 300 is in a fault state. In response to detecting such a fault state, the safety monitor 316 may be configured to cause the relevant input device to transition to a safe state. In some cases, the safety monitor 316 may be configured to cause the relevant input device to transition to a safe state by causing the safety device 314 to filter all communications between the relevant input device and the main controller.

As described above, the display of the operator console may be used or provide the user with a live image stream of the surgical site captured by an image capture device, such as, but not limited to an endoscope, or a representation thereof. In some cases, the display of the operator console may also be used to provide the user with a graphical user interface that allow the user to make configuration and other changes to the system. In some cases, when an input device (e.g. hand controller) is not in the engaged state (e.g. it is not being used to control a surgical robot arm) it may be used to provide input to the system via the graphical user interface. In some cases, when the display is in a mode in which it is displaying a graphical user interface, or an aspect of a graphical user interface, in which the user can make changes to the system, such as but not limited to, a user interface menu, none of the input devices should be in the engaged mode. In such cases, the safety monitor 316 may be configured to verify, from the communications to and from, the main controller that if the display device is in a mode in which it is display a graphical user interface, or an aspect of a graphical user interface, in which the user can make changes to the system that all of the input devices are in the disengaged state. If the safety monitor determines that when the display is in such as state that an input device is still indicating that it is engaged, the safety monitor 316 may determine that the surgical robot system 300 is in a fault state. In response to detecting such a fault state, the safety monitor 316 may be configured to cause the relevant input device to transition to a safe state. In some cases, the safety monitor 316 may be configured to cause the relevant input device to transition to a safe state by causing the safety device 314 to filter all communications between the relevant input device and the main controller.

As described above, in some cases, the input device (e.g. hand controllers) may comprise a first controller (which may be referred to as the handgrip arm base controller (HABC)) that generates input post information from the inputs and provides this to this information to the main controller 312. In some cases, each input device may also have a second controller (which may be simply referred to as the hand controller (HC)) that receives inputs from the operator and provides those inputs to the first controller (e.g. HABC). In some cases, the first controller (e.g. HABC) may also provide information on the status of the second controller (e.g. HC) to the main controller in addition to providing a copy of at least a portion of the raw information. In these cases, the safety monitor 316 also be configured to determine from the communication to and from the main controller, whether the second controller (e.g. HC) of an input device is reporting a fault, but the first controller does not report a fault. If the safety monitor 316 identifies such a discrepancy, the safety monitor 316 may determine that the surgical robot system 300 is in a fault state. In response to detecting such a fault state, the safety monitor 316 may be configured to cause the relevant input device to transition to a safe state. In some cases, the safety monitor 316 may be configured to cause the relevant input device to transition to a safe state by causing the safety device 314 to filter all communications between the relevant input device and the main controller.

In some cases, in addition to outputting the calculated input device pose, each input device may also output the joint angle(s) of the input device from which the input device pose was calculated. In these cases, the safety monitor 316 may also be configured to confirm the calculations performed by the input devices (e.g. the controllers thereof). For example, the safety monitor 316 may be configured to determine there is a fault state if the safety monitor 316 determines from the communication to and from the main controller 312 that the input device pose calculated by an input device controller is inconsistent with any input device joint angle by more than a predetermined amount (e.g. 0.1 degree). If the safety monitor 316 determines that the pose output by the input device controller is inconsistent then the safety monitor 316 may cause the relevant input device controller to transition to a safe state. In some cases, the safety monitor 316 may be configured to cause the relevant input device to transition to a safe state by causing the safety device 314 to filter all communications between the relevant input device controller and the main controller.

Energised Instrument Monitoring

In some cases, there may be special fault states when an energised instrument, such as an electrosurgical instrument, is attached to a surgical robot arm. An energised instrument is an instrument that can be energised by electrical energy such as an electrical current to perform a surgical procedure such as, but not limited to, cutting or cauterising.

In some cases, a surgical robot arm with an energised instrument attached thereto may be configured to periodically send out time-stamped tokens to the main controller 312. Upon receiving a token the main controller 312 may be configured to generate a modified token, which may be referred to as a valid token, and passes the valid token to the input device controller. If the input device receives an input from the operator that the energised instrument is to be energised (e.g. by pressing a special button on the input device) then the input device controller may send the valid token back to the main controller 312. If the main controller determines that the relevant surgical robot arm is engaged, then the main controller may send the valid token to the relevant surgical robot arm which will energise the energised instrument in response to receiving the valid token. This token-based activation method of an energised instrument is described in the Applicant's co-pending UK Patent applications 1803379.5 and 1902811.7, which are herein incorporated by reference in their entirety.

In these cases, the safety monitor 316 may be configured to detect, from the communications to and from the main controller, if the main controller sends a valid token to a surgical robot arm that does not match a valid token that was received from an input device (e.g. an input device controller) within a predetermined period (e.g. 3 milliseconds). If the safety monitor 316 detects that a transmitted valid token does not match a received valid token, then the safety monitor 316 may determine that the surgical robot system in in a fault state. In response to detecting such a fault state the safety monitor 316 may be configured to cause the relevant input device (e.g. input device controller) to transition to a safe state. In some cases, the safety monitor 316 may be configured to cause the relevant input device (e.g. input device controller) to transition to a safe state by causing the safety device 314 to filter all communications between the relevant input device (e.g. input device controller) and the main controller.

In these cases, the safety monitor may be configured to detect, from the communications to and from the main controller 312, if the main controller sends a valid token to a surgical robot arm that is not lined to an input device. If the safety monitor 316 detects that the main controller has send a valid token to a surgical robot arm that is not linked to an input device, the safety monitor 316 may determine that the surgical robot system 300 is in a fault state. In response to detecting such a fault state the safety monitor 316 may be configured to cause the relevant surgical robot arm (e.g. arm controller) to transition to a safe state. In some cases, the safety monitor 316 may be configured to cause the relevant surgical robot arm (e.g. arm controller) to transition to a safe state by causing the safety device 314 to filter all communications between the relevant surgical robot arm (e.g. arm controller) and the main controller.

In these cases, the safety monitor 316 may be configured to detect, from the communications to and from the main controller 312, if an input device (e.g. input device controller) transmits a valid token to the main controller 312 when the user has not indicated that the energised instrument is to be energised (e.g. when the user has not pressed the special energise button on the hand controller). If the safety monitor 316 detects that an input device transmits a valid token without the user indicating the energised instrument is to be energised, then the safety monitor 316 may determine that the surgical robot system 300 in in a fault state. In response to detecting such a fault state the safety monitor 316 may be configured to cause the relevant input device (e.g. input device controller) to transition to a safe state. In some cases, the safety monitor 316 may be configured to cause the relevant input device (e.g. input device controller) to transition to a safe state by causing the safety device 314 to filter all communications between the relevant input device (e.g. input device controller) and the main controller.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein. In view of the foregoing description it will be evident to a person skilled in the art that various modifications may be made within the scope of the invention.

The invention claimed is:

1. A control system for controlling a surgical robot system, the surgical robot system comprising a surgical robot, the surgical robot comprising a base, and an arm extending from the base to an attachment for an instrument, the arm comprising a plurality of joints whereby the configuration of the arm can be altered, the control system comprising:

a main controller configured to:
    receive communications identifying inputs from an operator of the surgical robot;
    generate control signals for controlling the movement of the surgical robot arm based on the inputs; and
    send communications to the surgical robot identifying the control signals; and
a safety device situated such that communications to and from the main controller pass through the safety device, the safety device being operable to selectively filter the communications to and/or from the main controller.

2. The control system of claim 1, wherein the safety device is configured to filter at least a portion of the communications to and/or from the main controller in response to the surgical robot system being in a fault state.

3. The control system of claim 1, wherein the safety device comprises one or more filters, and the one or more filters are configured to filter the communications to and/or from the main controller by comparing received communications to one or more filter criteria.

4. The control system of claim 3, wherein the one or more filters comprises a receive filter and the one or more filter criteria comprises one or more receive filter criteria, the receive filter configurable to filter the communications from the main controller by comparing the communications from the main controller to the one or more receive filter criteria.

5. The control system of claim 4, wherein the receive filter comprises a buffer to store the communications received from the main controller.

6. The control system of claim 5, wherein the receive filter comprises a manifold and one or more matchers, the manifold configured to extract relevant information from the received communications prior to storing the received communications in the buffer, and the one or more matchers are configured to compare the relevant information to the one or more receive filter criteria.

7. The control system of claim 4, wherein the one or more filter criteria comprises one or more transmit filter criteria and the at least one filter comprises a transmit filter, the transmit filter being configurable to filter the communications to the main controller by comparing the communications to the main controller to the one or more transmit filter criteria.

8. The control system of claim 7, wherein the transmit filter comprises a buffer to store the communications to the main controller.

9. The control system of claim 8, wherein the transmit filter comprises a manifold and one or more matchers, the manifold configured to extract relevant information from the communications to the main controller prior to storing the communications to the main controller in the buffer, and the one or more matchers are configured to compare the relevant information to the one or more transmit filter criteria.

10. The control system of claim 7, wherein the one or more transmit filter criteria comprises up to K receive filter criteria, wherein K is an integer based on a number of comparisons that can be performed between a communication and a filter criteria in a cycle and a number of cycles it takes to receive a communication.

11. The control system of claim 3, wherein the one or more receive filter criteria comprises up to N receive filter criteria, wherein N is an integer based on a number of comparisons that can be performed between a communication and a filter criteria in a cycle and a number of cycles it takes to receive a communication.

12. The control system of claim 3, wherein the one or more filter criteria is configurable.

13. The control system of claim 12, wherein the one or more filter criteria is configurable to cause the safety device to filter all communications to and from the main controller.

14. The control system of claim 12, wherein the one or more filter criteria is configurable to cause the safety device to filter communications between the main controller and a specific device in the surgical robot system.

15. The control system of claim 3, wherein each of the one or more filter criteria comprises one or more of a source address, destination address, source port and destination port.

16. The control system of claim 3, wherein the one or more filters are configured to, in response determining that a communication matches at least one of the one or more filter criteria, reject the communication.

17. The control system of claim 16, wherein the one or more filters are configured to reject the communication by discarding the communication.

18. The control system of claim 16, wherein the one or more filters are configured to reject the communication by corrupting the communication.

19. The control system of claim 1, further comprising a safety monitor and the safety device is configured to send a copy of at least a portion of the communications to and/or from the main controller to the safety monitor.

20. A method of selectively filtering communications to and/or from of a main controller of a surgical robot system, the surgical robot system comprising a surgical robot, the surgical robot comprising a base, and an arm extending from the base to an attachment for an instrument, the arm comprising a plurality of joints whereby the configuration of the arm can be altered, the main controller configured to receive communications identifying inputs from an operator of the surgical robot, generate control signals for controlling the movement of the surgical robot arm based on the inputs, and send communications to the surgical robot identifying the control signals, the method comprising:

receiving at a safety device a communication to or from the main controller;
determining whether at least one filter criteria has been specified;
in response to determining that at least one filter criteria has been specified, comparing the received communication to the at least one specified filter criteria;
in response to determining that the received communication matches at least one of the at least one filter criteria, rejecting the received communication; and
in response to determining that the received communication does not match any of the at least one filter criteria, outputting the received communication to the relevant device.

* * * * *